(12) United States Patent
Reynard

(10) Patent No.: US 12,727,758 B1
(45) Date of Patent: Sep. 8, 2026

(54) SYSTEM AND METHOD FOR AI-ENHANCED RAMAN SPECTROSCOPY TEAR ANALYSIS

(71) Applicant: Michael Reynard, Santa Monica, CA (US)

(72) Inventor: Michael Reynard, Santa Monica, CA (US)

(*) Notice: Subject to any disclaimer, the term of this patent is extended or adjusted under 35 U.S.C. 154(b) by 0 days.

(21) Appl. No.: 19/260,723

(22) Filed: Jul. 7, 2025

(51) Int. Cl.

| | |
|---|---|
| ***A61B 3/10*** | (2006.01) |
| ***A61B 5/00*** | (2006.01) |
| ***A61B 5/145*** | (2006.01) |
| ***A61B 5/1455*** | (2006.01) |
| ***A61B 10/00*** | (2006.01) |
| ***G01N 21/65*** | (2006.01) |
| ***G01N 33/487*** | (2006.01) |
| ***G16H 40/63*** | (2018.01) |
| ***G16H 50/20*** | (2018.01) |

(52) U.S. Cl.
CPC .......... *A61B 3/101* (2013.01); *A61B 5/14532* (2013.01); *A61B 5/14546* (2013.01); *A61B 5/1455* (2013.01); *A61B 5/7267* (2013.01); *A61B 10/0045* (2013.01); *G01N 21/65* (2013.01); *G01N 33/487* (2013.01); *G16H 40/63* (2018.01); *G16H 50/20* (2018.01); *A61B 2010/0067* (2013.01); *A61B 2560/0431* (2013.01); *A61B 2560/0443* (2013.01)

(58) Field of Classification Search
CPC ............ A61B 3/101; A61B 2010/0067; A61B 5/14546; A61B 5/1455; A61B 5/7267; G01N 33/487; G01N 21/65; G16H 50/20
See application file for complete search history.

(56) References Cited

U.S. PATENT DOCUMENTS

| | | | |
|---|---|---|---|
| 6,721,583 | B1 | 4/2004 | Durkin et al. |
| 7,395,103 | B2 | 7/2008 | Cappo et al. |

(Continued)

FOREIGN PATENT DOCUMENTS

| | | | |
|---|---|---|---|
| BR | 112021001576 | A2 | 4/2021 |
| CA | 2757486 | A1 | 10/2010 |

(Continued)

OTHER PUBLICATIONS

Park, M., et al. Plasmonic Schirmer Strip for Human Tear-Based Gouty Arthritis Diagnosis Using Surface-Enhanced Raman Scattering. ACS Nano. 2016 (Year: 2016).*

(Continued)

*Primary Examiner* — Eric F Winakur
*Assistant Examiner* — Sienna C Pyle
(74) *Attorney, Agent, or Firm* — Richard A Baker, Jr.

(57) ABSTRACT

A modular diagnostic system is disclosed for acquiring Raman spectral data from tear film and analyzing biochemical signatures using Artificial Intelligence (AI). The system includes a Raman excitation source, a spectral acquisition module, and a processing engine configured to perform baseline correction, feature extraction, and AI-based classification. The system enables real-time, non-invasive diagnostics for dry eye disease, diabetes, metabolic disease, pharmacologic agents, and other conditions. The system supports longitudinal tracking and EMR integration. Real-time outputs support clinical diagnosis, treatment guidance, and longitudinal monitoring.

25 Claims, 9 Drawing Sheets

(56) References Cited

U.S. PATENT DOCUMENTS

| | | | | |
|---|---|---|---|---|
| 7,557,915 | B2 | 7/2009 | Maier et al. | |
| 7,987,702 | B2 | 8/2011 | Sullivan | |
| 8,531,660 | B2 | 9/2013 | Dziecielewski et al. | |
| 9,278,120 | B2 | 3/2016 | Cruzat et al. | |
| 9,335,243 | B2 | 5/2016 | Donsky et al. | |
| 9,442,065 | B2 * | 9/2016 | Gulati | A61B 5/7264 |
| 9,733,125 | B2 | 8/2017 | Liu et al. | |
| 11,016,025 | B2 | 5/2021 | Gavaris et al. | |
| 11,307,092 | B2 | 4/2022 | Atabaki et al. | |
| 11,536,707 | B2 | 12/2022 | Sullivan et al. | |
| 11,771,217 | B2 | 10/2023 | Tseng et al. | |
| 12,318,195 | B2 | 6/2025 | Jue et al. | |
| 2007/0224683 | A1 * | 9/2007 | Clarke | G01N 21/65 356/301 |
| 2015/0351628 | A1 | 12/2015 | Huth et al. | |
| 2017/0181645 | A1 * | 6/2017 | Mahalingam | A61B 5/74 |
| 2017/0234798 | A1 | 8/2017 | Choi et al. | |
| 2022/0313077 | A1 | 10/2022 | Singh et al. | |
| 2024/0266016 | A1 * | 8/2024 | Mirkar | G16H 30/20 |
| 2024/0371496 | A1 * | 11/2024 | Wang | G16H 20/70 |

FOREIGN PATENT DOCUMENTS

| | | | | |
|---|---|---|---|---|
| CN | 116559143 | A * | 8/2023 | G01N 21/65 |
| WO | WO-2008141306 | A2 * | 11/2008 | A61B 5/14532 |
| WO | 2019200535 | A1 | 10/2019 | |
| WO | WO-2022120225 | A1 * | 6/2022 | A61B 5/088 |

OTHER PUBLICATIONS

Schie et al. Looking for a perfect match multimodal combinations of Raman spec for biomed 2021 (Year: 2021).*

Wei, D., et al., Review of Fluorescence Suppression Techniques in Raman Spectroscopy. Applied Spectroscopy Reviews, 2015 (Year: 2015).*

Wu, J., et al., Rapid diagnosis of diabetes based on ResNet and Raman spectroscopy, Photodiagnosis and Photodynamic Therapy, 2022 (Year: 2022).*

Shao J, Lin M, Li Y, et al. In vivo blood glucose quantification using Raman spectroscopy. PLoS One. 2012 (Year: 2012).*

Cacace, T., Posa, M., De Santo, M. P., & Silvestri, B. (2019). Application of Raman Microspectroscopy to Evaluate Tear Film Biochemistry in Ocular Surface Disease. Current Eye Research, 44(9), 957-963. https://doi.org/10.1080/02713683.2019.1602986.

Camerlingo C, Lisitskiy M, Lepore M, Portaccio M, Montorio D, Prete SD, Cennamo G. Characterization of Human Tear Fluid by Means of Surface-Enhanced Raman Spectroscopy. Sensors. 2019; 19(5):1177. https://doi.org/10.3390/s19051177.

Filik, J., N. Stone, Analysis of human tear fluid by Raman spectroscopy, Analytica Chimica Acta, vol. 616, Issue 2, 2008, pp. 177-184, ISSN 0003-2670, https://doi.org/10.1016/j.aca.2008.04.036.

Guo, Z., Ma, M., Lu, S., Ma, Y., Yu, Y., Guo, Q. Applications of Raman Spectroscopy in Ocular Biofluid Collection. Front. Chem., Jun. 9, 2024, vol. 12-2024. https://doi.org/10.3389.fchhem.2024.1407754.

Thomas, K. M., Ajithaprasad, S., Mithun, N., Pavithran, S., Chidangil, S., & Lukose, J. (2024). Raman Spectroscopy Assisted Tear Analysis: a Label-Free, Optical Approach for Noninvasive Disease Diagnostics. Experimental Eye Research, 243, 109913. https://doi.org/10.1016/j.exer.2024.109913.

Lebedev, A. T., Nikolaev, E. N., & Ivanov, A. S. (2015). Surface-Enhanced Raman Spectroscopy of Biofluids: Towards Clinical Diagnosis. Journal of Raman Spectroscopy, 46(12), 1165-1177. https://doi.org/10.1002/jrs.4819.

Lyng, F. M., Faolain, E. Ó., & Byrne, H. J. (2004). Vibrational Spectroscopy for Cancer Detection in Biofluids. Biochimica et Biophysica Acta (BBA)—Reviews on Cancer, 1700(1), 123-131. https://doi.org/10.1016/j.bbcan.2004.03.002.

Notingher, I. (2007). Raman Spectroscopy Cell-Based Biosensors. Sensors, 7(8), 1343-1358. https://doi.org/10.3390/s7081343.

Pieczynski, J., Mehta, J. S., Chaurasia, S. S., & Tan, D. T. H. (2012). Diurnal Variation of Human Tear Fluid Components Measured Using HPLC and LC-MS/MS. Molecular Vision, 18, 2283-2291.

Qi, Y., Wang, Y., & Wang, J. (2021). Detection of Glucose and Lactoferrin in Human Tear Using SERS. Sensors and Actuators B: Chemical, 331, 129353. https://doi.org/10.1016/j.snb.2020.129353.

Subash, M., Barathi, V. A., & Beuerman, R. W. (2017). Comparative Study of Inflammatory Cytokines in Tears of Patients with Dry Eye Syndrome. Ocular Immunology and Inflammation, 25(5), 499-505. https://doi.org/10.1080/09273948.2016.1171117.

Zhou, L., Beuerman, R. W., Barathi, A., & Tan, D. (2009). Analysis of Rabbit Tear Proteins by High-Pressure Liquid Chromatography and Electrospray Tandem Mass Spectrometry. Investigative Ophthalmology & Visual Science, 50 (10), 4819-4831. https://doi.org/10.1167/iovs.08-3090.

Wu, J., Zheng, Y., & Liu, Y. (2015). Raman Spectroscopy and Chemometric Methods for Quantitative Analysis of Tear Film Components. Analytical Chemistry, 87(17), 9056-9063. https://doi.org/10.1021/acs.analchem.5b01763.

Yoon, K. C., Jeong, I. Y., Park, Y. G., & Yang, S. Y. (2012). Interleukin-6 and Tumor Necrosis Factor-α Level in Tears of Patients with Dry Eye Syndrome. Cornea, 31(9), 994-998. https://doi.org/10.1097/ICO.0b013e3182419c55.

Capaccio, Angela; Sasso, Antonio; and Rusciano, Giulia. Raman Analysis of Tear Fluid Alteration Following Contact Lense Use. Sensors 2019, 19, 3392; doi:10.3390/s19153392.

Rolandi, R., Duse, A., Tavazzi, S., Grandori, R., Pezzoli, F., & Ponzini, E. (2024). Raman spectroscopy to investigate early biochemical alterations in human tears caused by contact lenses. Clinical and Experimental Optometry, 108(1), 14-20. https://doi.org/10.1080/08164622.2024.2419981.

Zhan, Xiamquan; Li, Jiajia; Guo, Yuna; Golubnitschaja, Olga. Mass spectrometry analysis of human tear fluid biomarkers specific for ocular and systemic diseases in the context of 3P medicine. EPMA Journal (2021) 12:449-475. https://doi.org/10.1007/s13167-021-00265-y.

Reyes-Goddard, J.; A. Woodman; N. Stone; H. Barr; J. A. Creighton; Y. Saito; and D. Batchelder, "Surface enhanced Raman scattering of the tear film," in Diagnostic Optical Spectroscopy in Biomedicine II, G. Wagnières, ed., vol. 5141 of Proc. SPIE (Optica Publishing Group, 2003), paper 5141_219.

* cited by examiner

Longitudinal trend monitoring interface with visual comparison of Raman spectra over time

SYSTEM AND METHOD FOR AI-ENHANCED RAMAN SPECTROSCOPY TEAR ANALYSIS

CROSS-REFERENCE TO RELATED APPLICATIONS

This is a priority application.

FIELD OF THE INVENTIONS

The present inventions relate to diagnostic technologies in ophthalmology and biomedical analytics, and more specifically to a system for non-invasive analysis of tear fluid using Raman spectroscopy integrated with artificial intelligence to identify, classify, and monitor disease-specific and treatment-related biomarkers.

BACKGROUND

Tear fluid contains a diverse range of biomolecules—lipids, proteins, cytokines, metabolites—that reflect both ocular surface health and systemic physiologic conditions. Conventional methods for diagnosing dry eye disease or systemic abnormalities rely on invasive sampling, subjective clinical tests, or time-consuming laboratory assays.

The disclosed system addresses this unmet need by integrating advanced spectral acquisition, machine learning interpretation, and modular diagnostic platforms designed for use in eye clinics, telemedicine environments, and research settings.

BRIEF SUMMARY

These inventions provide a flexible, modular, and AI-enhanced Raman spectroscopy system for tear-based diagnostics. It enables real-time classification and monitoring of ocular and systemic diseases by detecting low-abundance biomarkers in tear fluid. The innovations include:

- Modular hardware and software architecture for easy integration and upgrading;
- AI pipeline with preprocessing, feature extraction, and classification layers;
- Longitudinal monitoring of disease progression through spectral tracking;
- Applicability to multiple diseases from a single tear sample;
- Enablement across various clinical settings, including telehealth and point-of-care.

In one aspect, a system for non-invasive biochemical analysis of tear fluid, includes a Raman excitation source that directs light to the tear fluid of a patient and creates Raman-scattered light as the light reflects off the tear fluid, a spectral acquisition module configured to detect the Raman-scattered light from the tear fluid and create Raman spectral data from the Raman-scattered light, a computer includes one or more artificial intelligence (AI) models configured to preprocess, extract features from, and classify the Raman spectral data to identify one or more biomarkers associated with ocular or systemic disease.

One or more artificial intelligence (AI) models may include a convolutional neural network (CNN) trained to classify spectral patterns in the Raman spectral data into diagnostic categories, including dry eye disease, diabetes, oxidative stress, or inflammatory conditions. The system may also include a longitudinal monitoring module configured to compare the Raman spectral data with previous Raman spectral data from the patient. The spectral acquisition module may include a non-contact optical head adapted for slit lamp integration to acquire Raman signals directly from the tear fluid. The system may also include a modular diagnostic cartridge containing a surface-enhanced Raman scattering (SERS) substrate and a tear-wicking membrane for collection of the tear fluid. The computer may further include a segmentation module configured to identify spectral windows corresponding to known biomarkers, including lactoferrin, glucose, MMP-9, or malondialdehyde. The Raman excitation source may operate at 785 nm, 830 nm, or 1064 nm. The spectral acquisition module may further include confocal optics for depth-resolved Raman signal capture. One or more artificial intelligence (AI) models may be configured to detect a level of glucose.

One or more artificial intelligence (AI) models may apply principal component analysis (PCA) or wavelet transforms for feature extraction. The one or more artificial intelligence (AI) models that classify may be updated via encrypted cloud-based training, incorporating clinician feedback. The computer may further include a contextual data module configured to adjust classification thresholds based on time of day or environmental conditions. The system may also include a user interface that presents spectral trend graphs for tracked biomarkers across multiple visits. The system may also be configured to detect pharmacologic agents or illicit substances present in tear fluid via Raman spectral signature comparison. The AI classification may include scoring for alcohol-related metabolite presence in tear samples.

The system may provide risk stratification for age-related macular degeneration based on oxidative stress markers in the tear fluid. The system may also include a swept-source excitation module configured to dynamically tune the laser wavelength based on target biomarker absorption characteristics. The system may be integrated into a wearable headset or goggle apparatus for telehealth deployment. The system may also be configured to detect cancer-related biomarkers such as lactate, cytochrome c, or DNA fragments in tear samples. The diagnostic output may include probability-weighted disease classifications and AI-generated treatment recommendations. The system may also be further configured to integrate Raman analysis results with ocular imaging data, including optical coherence tomography or infrared reflectance. The Raman spectral data may be annotated with time-series metadata for use in trend forecasting or anomaly detection. The system may perform analysis on the tear fluid in a non-clinical setting via a mobile device platform with real-time AI feedback.

In one aspect, a method for diagnosing disease based on tear fluid analysis, includes collecting a tear sample from a patient, illuminating the tear sample with a Raman excitation source, detecting Raman-scattered light from the Raman excitation source reflected off of the tear sample, converting the Raman-scattered light into spectral data, processing the spectral data using an AI model configured to classify the patient into one or more diagnostic categories.

The AI model may be configured to classify the patient as having an excessive level of glucose. The AI model may be trained using a dataset of more than 10,000 annotated tear spectra labeled by disease condition. The one or more diagnostic categories may include one or more of: dry eye subtypes, systemic inflammation, neurodegenerative disease, or metabolic disorders. The AI analysis may include subtyping of dry eye disease into evaporative, aqueous-deficient, or inflammatory categories. The tear samples may be collected via Schirmer strip, hydrogel pad, or direct in situ scanning. The preprocessing may include baseline correction, Savitzky-Golay smoothing, and fluorescence suppression. The classification may be achieved using a random forest, support vector machine, or ensemble model.

In one aspect, a portable tear analysis device includes a Raman spectroscopy module configured to direct light onto tear film of a patient, creates Raman-scattered light as the light reflects off the tear film, detects the Raman-scattered light from the tear film, and creates Raman spectral data from the Raman-scattered light, a computer includes one or more artificial intelligence (AI) models an AI processing unit housed within the portable tear analysis device configured to preprocess, extract features from, classify the Raman spectral data to identify one or more biomarkers associated with ocular or systemic disease, and determine diagnostic or monitoring results, and a display configured to output the diagnostic or monitoring results in real time to a clinician or patient. Other technical features may be readily apparent to one skilled in the art from the following figures, descriptions, and claims.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Figure 1:
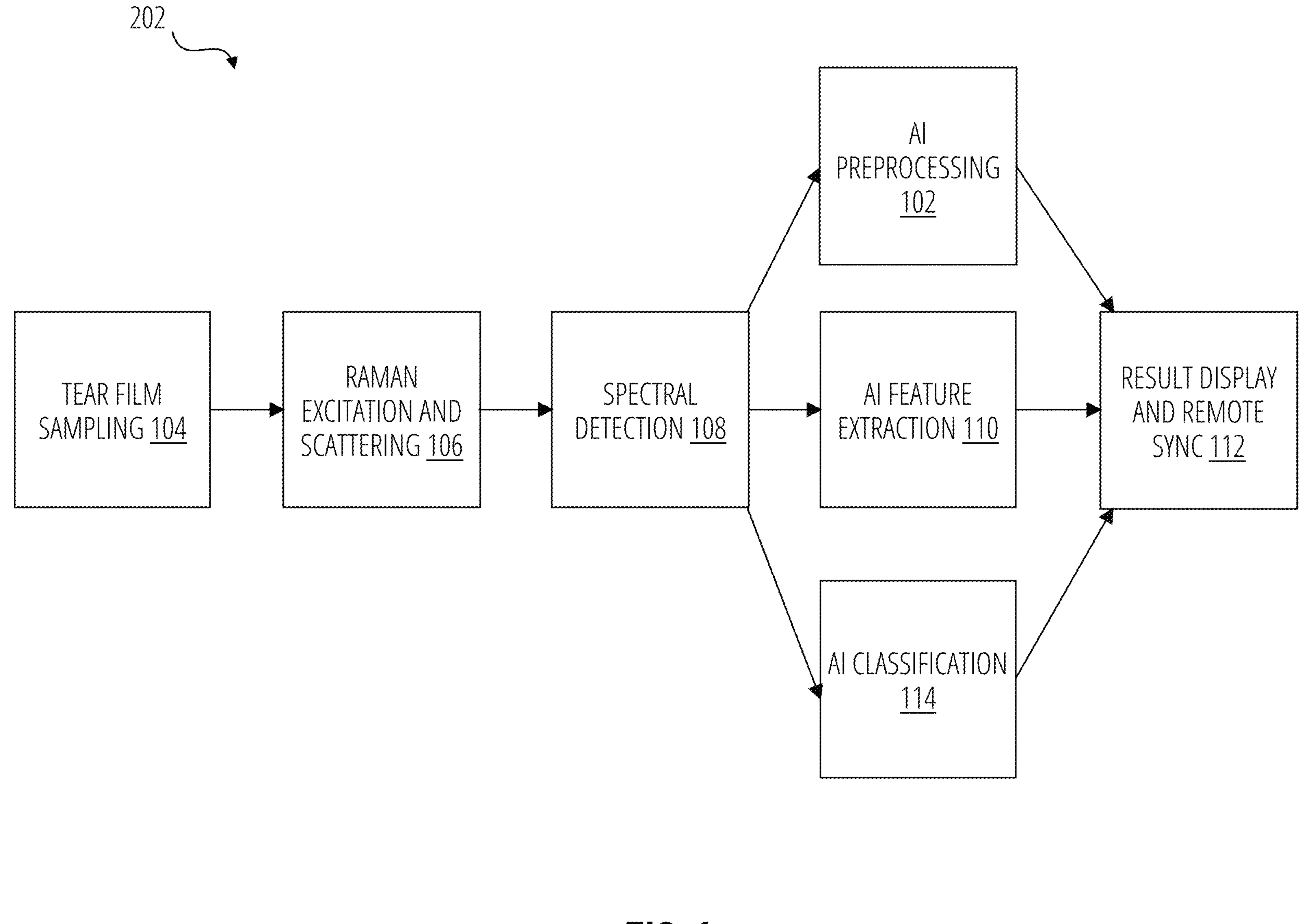
FIG. 1 is a flowchart representation of the modular AI-enhanced Raman tear diagnostic system, showing integration of tear collection, Raman acquisition, and AI computational modules.

All illustrations of the drawings are for the purpose of describing selected versions of the present inventions and are not intended to limit the scope of the present inventions.

The disclosed AI-enhanced Raman spectroscopy tear analysis system 202 is enabled through a multilayered architecture that supports spectral preprocessing 102, 504, pattern segmentation, feature extraction 110, 506, and probabilistic classification of tear biomarkers 114, 508. Core functional modules of the AI system include:

Spectral Preprocessing Layer 102, 504: This component normalizes raw Raman spectra through baseline correction, noise suppression (e.g., Savitzky-Golay smoothing), and signal enhancement to ensure uniform quality of input data across varying patient conditions and sample volumes.

Segmentation Module: The segmentation engine 918 identifies distinct regions of interest (ROI) within the Raman spectrum corresponding to known biochemical classes (e.g., proteins, lipids, small molecules). It applies techniques for spectral detection 108 such as peak detection algorithms, derivative analysis, and adaptive windowing to isolate meaningful intervals for subsequent AI analysis.

Feature Extraction and Dimensionality Reduction 110, 506: This module converts segmented data into quantitative features using principal component analysis (PCA), independent component analysis (ICA), or wavelet transforms. These features reduce spectral complexity while preserving diagnostically relevant signatures.

Classifier Layer 114, 508: A supervised machine learning model (e.g., random forest, support vector machine, or convolutional neural network) maps extracted features to diagnostic categories or biomarker concentrations. Training is performed on annotated datasets containing spectral profiles from normal and diseased tear film samples. Representative training datasets may include over 10,000 Raman spectra acquired from tear film samples labeled by disease category (e.g., dry eye, diabetes, pharmacologic exposure). Labeling may be based on clinical diagnosis, osmolarity testing, or physician confirmation.

Training Environment and Tools: The AI models may be developed using frameworks such as TensorFlow or PyTorch and trained in a cloud environment or GPU-enabled workstation using standard cross-validation and stratified sampling to ensure generalizability across patient cohorts.

Cross-Modality Integration: Optionally, the AI system may be configured to integrate Raman outputs with secondary inputs, such as environmental metadata (e.g., humidity, time of day) or ocular surface imaging, improving diagnostic specificity.

Adaptive Learning Engine 208: Over time, the system refines its predictions via federated learning or cloud-based model updates, incorporating clinician-confirmed outcomes to enhance diagnostic robustness and personalization. The AI module may be updated securely through encrypted firmware uploads or cloud-managed services.

Deployment Configurations: The artificial intelligence engine 828 may operate on-device using embedded chipsets for real-time processing, or remotely through cloud-based platforms, enabling scalability across clinical and point-of-care environments. In either case, latency is optimized to support diagnostic use during live ocular examination.

Expected Performance: In clinical configurations, the AI classifier is expected to achieve a minimum of 90% sensitivity and 85% specificity for major diagnostic classes based on internal validation datasets. These thresholds are adjustable depending on the application (e.g., screening vs. confirmation).

Hypothetical Example: For example, a Raman spectrum showing elevated peaks at 600 $cm^{-1}$ (lactoferrin) and reduced lipid-associated intensity at 1400 $cm^{-1}$ may be classified by the artificial intelligence engine 828 as indicative of evaporative dry eye. The same AI-enhanced Raman spectroscopy tear analysis system 202 may detect abnormal protein-lipid ratios consistent with tear film instability following ocular medication use.

Noise Reduction 102, 504: Noise reduction is a meaningful preprocessing step in the AI pipeline to enhance the clarity and fidelity of Raman spectral signals. The raw spectra may contain background fluorescence, electronic noise, and sampling artifacts that obscure subtle biomolecular peaks. The AI-enhanced Raman spectroscopy tear analysis system 202 applies smoothing filters such as Savitzky- Golay, wavelet denoising, or polynomial fitting to attenuate random noise while preserving true spectral features. This ensures cleaner inputs for downstream segmentation and classification, improving signal-to-noise ratio and diagnostic reliability.

Feature Extraction 110, 506: Feature extraction transforms processed spectral data into condensed representations that retain meaningful diagnostic information. Following segmentation, techniques such as Principal Component Analysis (PCA), Independent Component Analysis (ICA), or wavelet decomposition are applied to reduce data dimensionality. These approaches isolate statistically independent or orthogonal components that correspond to variations in biomarker concentration or molecular structure. Extracted features form the core input to the classifier engine and allow for rapid, scalable comparisons across patient datasets.

Classifier Engine 114, 508: The classifier engine is the AI module responsible for mapping extracted features to diagnostic outputs. It utilizes supervised machine learning algorithms, including convolutional neural networks (CNNs), support vector machines (SVMs), or random forests, trained on labeled spectral datasets representing healthy and diseased tear profiles. The classifier computes probability-weighted predictions for each class (e.g., dry eye, diabetes, normal), enabling real-time decision support. The engine is continually refined through cross-validation, clinician feedback, and cloud-based updates to improve accuracy across diverse populations.

Region of Interest (ROI) Isolation Region of Interest (ROI) Isolation is a key step in the AI processing pipeline for Raman spectroscopy and plays a central role in ensuring diagnostic accuracy. In this AI-enhanced Raman spectroscopy tear analysis system 202, ROI Isolation refers to the automated identification and selection of specific spectral intervals or features within the full Raman spectrum that are most relevant for clinical interpretation, particularly those associated with known biomarkers or disease-specific molecular signatures.

In the context of the AI-enhanced Raman spectroscopy tear analysis system 202, the full Raman spectrum may contain hundreds or thousands of data points. ROI Isolation enables the AI system to focus only on meaningful segments (e.g., 990-1005 $cm^{-1}$ for lysozyme or 1080-1120 $cm^{-1}$ for glucose). This targeted focus enhances the efficiency, accuracy, and interpretability of subsequent AI-based classification and diagnostic decision-making.

The AI-enhanced Raman spectroscopy tear analysis system 202 uses a combination of spectral segmentation tools and algorithmic filters to execute ROI Isolation. Techniques include peak detection algorithms, thresholding and window-based filters, spectral windowing with dynamic range focus, derivative-based feature enhancement, and baseline spectral comparison to detect abnormalities These techniques ensure that diagnostically relevant intervals are not only identified but prioritized in the AI interpretation pipeline, thereby supporting reliable, real-time biomarker classification across varied patient populations.

These modules collectively enable real-time, automated interpretation of Raman spectra with high clinical relevance. The segmentation functionality, in particular, supports adaptability to both disease-specific and pharmacologic biomarker targets, facilitating diagnostic expansion across ocular and systemic domains.

Clinical Value of AI-Enhanced Raman Spectroscopy in Tear Analysis

Tear fluid represents an exceptionally rich, yet underutilized, medium for non-invasive diagnostic investigation. Compared to blood or aqueous humor collection, tear sampling offers a significantly less invasive alternative that is particularly well-suited for sensitive populations, including children, the elderly, and patients with ocular surface disorders such as dry eye disease. This non-invasiveness allows for routine screening and longitudinal monitoring without causing discomfort or disrupting ocular physiology.

The tear film itself is a complex and informative biological fluid, composed of lipids, proteins, cytokines, metabolites, and electrolytes that reflect both local ocular pathology and systemic disease states. Raman spectroscopy, particularly in its surface-enhanced (SERS) format, enables the sensitive detection of these molecular components. It can differentiate disease signatures based on unique molecular vibrations, making it ideal for identifying conditions such as diabetes, dry eye syndrome subtypes, neurodegenerative disease, and cancer through tear analysis alone.

What distinguishes the AI-enhanced Raman spectroscopy tear analysis system 202 is the integration of AI-driven spectral processing into this Raman platform. Artificial intelligence not only assists in denoising and environmental correction but also performs segmentation and feature extraction that map complex spectra into identifiable biomarker profiles. The use of AI dramatically enhances specificity and sensitivity, allowing the system to detect minute concentrations of diagnostic molecules that would otherwise be obscured by baseline noise or biological variability. In real-time applications, this AI-driven interpretation transforms a raw Raman spectrum into clinically actionable output within seconds.

Raman spectroscopy has the capacity to detect tear-based markers such as glucose, lactate, and urea, track inflammatory mediators like IL-1 and TNF-$\alpha$, and identify protein fingerprints associated with multiple sclerosis and oncologic processes. The addition of AI stratification extends this utility by enabling robust classification even in the presence of confounding variables such as pH fluctuation, osmolarity shifts, or tear volume inconsistency. Further, the microfluidic SERS cartridge, embedded with environmental sensors and optimized for Raman signal yield, ensures high reproducibility and sampling efficiency.

Challenges associated with tear diagnostics, including low analyte concentrations, inter-patient variability, and the need for signal standardization, are addressed through a combination of smart design and algorithmic intelligence. By coupling hardware innovations with AI-enhanced spectral interpretation, the AI-enhanced Raman spectroscopy tear analysis system 202 delivers a compact, scalable, and non-invasive diagnostic solution with immediate clinical relevance across ophthalmology, endocrinology, neurology, and forensic applications.

The system's AI-enhanced analysis not only improves specificity and sensitivity but also compensates for inter-patient variability, environmental conditions, and collection inconsistencies such as tear volume or osmolarity shifts. The microfluidic SERS cartridge further supports this precision by offering controlled sampling, embedded environmental sensors, and reproducible signal enhancement. These features, in combination, streamline the diagnostic process into a point-of-care modality suitable for rapid clinical deployment.

The platform is designed to support a wide array of clinical applications, from ophthalmology to endocrinology, neurology, and even forensic screening. It allows immediate classification of disease subtypes, guides therapeutic decisions, and supports longitudinal tracking of disease progression or response to treatment. By bridging molecular precision with real-time algorithmic interpretation, the AI-enhanced Raman spectroscopy tear analysis system 202 represents a paradigm shift in the accessibility and utility of biochemical diagnostics at the point of care.

FIG. 1 shows a schematic representation of the modular AI-enhanced Raman spectroscopy tear analysis system 202, showing integration of tear collection, Raman acquisition, and AI computational modules.

This integrative flow chart depicts the processing sequence of the AI-enhanced Raman spectroscopy tear analysis system 202. It begins with non-contact tear film sampling 104 and progresses through Raman excitation and scattering 106, spectral detection 108, and layered AI processing, including AI preprocessing 102, AI feature extraction 110, and AI classification 114. The result display and remote sync 112 is then presented to the user. Diagnostic outputs are presented on a local or mobile display and may be synchronized with cloud-based records or mobile apps.

The tear film sampling 104 may collect and label patient 212 tears and control samples. The Raman excitation and scattering 106 may then use a 785 nm laser 804 to acquire Spectra (spectral detection 108) from the tear fluid. The AI preprocessing 102 then may use signal processing techniques, either in software or hardware, to reduce noise, normalize, and make baseline corrections. The AI feature extraction 110 may then use a CNN to identify peaks and ratios (e.g. 1450/1655 $cm^{-1}$). The AI classification 114 may then calculate a Softmax layer output dry eye probability score and classify the sample according to the score. And the result display and remote sync 112 may diagnose the eye according to the probability score.

Figure 2:
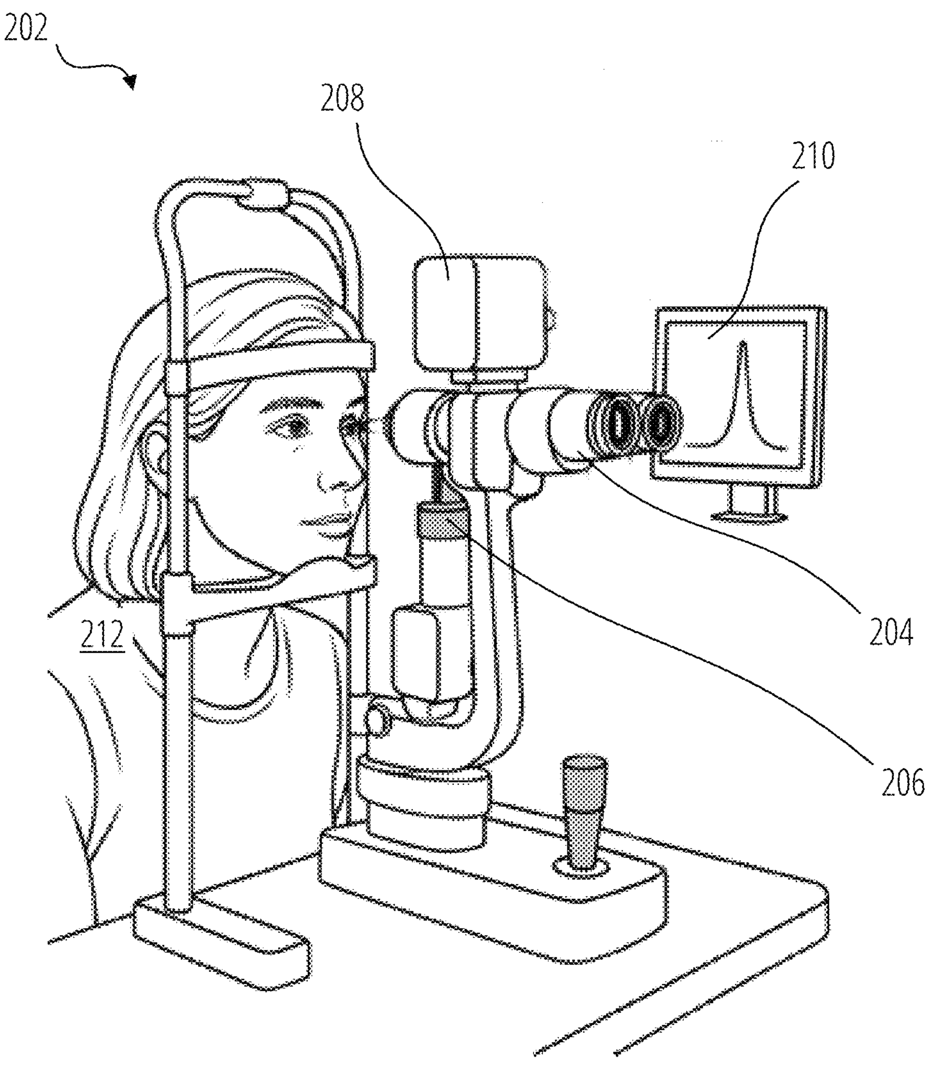
FIG. 2 shows an AI-Enhanced Raman Spectroscopy for Non-Contact Tear Analysis at the Slit Lamp.

FIG. 2 depicts an embodiment of the AI-enhanced Raman spectroscopy tear analysis system 202 integrated with a slit lamp 204. The Raman module 206 is mounted adjacent to the slit lamp 204 optics and positioned to acquire spectral data from the ocular surface. A dedicated AI processing unit 208 is co-mounted on the slit lamp 204 frame, enabling real-time analysis and diagnostic output. A nearby display screen 210 presents diagnostic output, including biomarker peaks from the patient's tear fluid.

Figure 3:
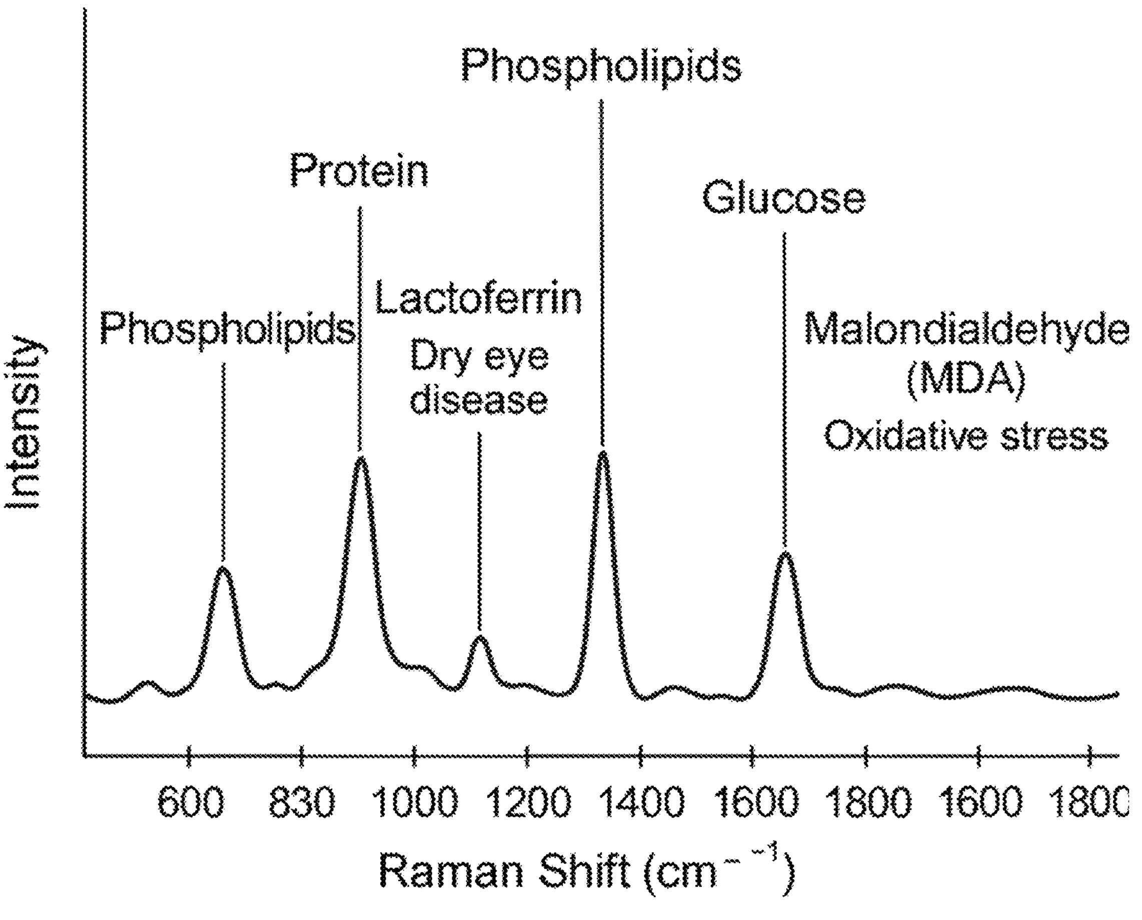
FIG. 3 is an Example Raman spectrum of tear fluid with labeled biomarker peaks relevant to dry eye disease, diabetes, and oxidative stress.

FIG. 3 is an example of a Raman Shift reading in tear fluid, showing peaks for Phospholipids, protein, lactoferrin (indicating dry eye disease), phospholipids, glucose, and malondialdehyde (MDA), indicating oxidative stress.

FIG. 3 maps key Raman shifts (in $cm^{-1}$) to specific biomolecular components detected in tear samples. Each entry includes the corresponding compound or functional group, peak assignment, and associated disease relevance. FIG. 3 highlights how spectral analysis of tear fluid can be used to detect inflammatory markers (e.g., MMP-9), metabolic changes (e.g., glucose), and oxidative stress indicators (e.g., MDA), enabling differential diagnosis or longitudinal monitoring of ocular and systemic conditions.

Figure 4:
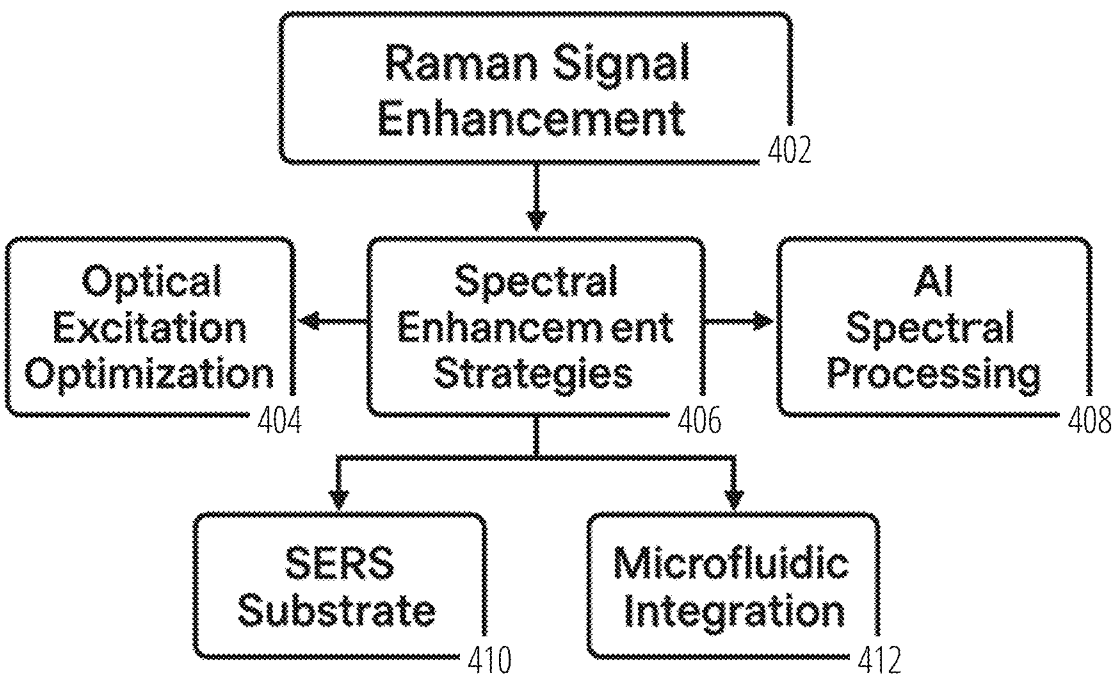
FIG. 4 illustrates the spectral enhancement strategies, including an optional SERS substrate and microfluidic integration.

FIG. 4 is a diagram illustrating the spectral enhancement strategies. These strategies include an optional SERS substrate and microfluidic integration. The diagram illustrates spectral enhancement strategies for Raman-based tear diagnostics. Key components include an optional surface-enhanced Raman scattering (SERS) substrate to amplify signal strength, and an integrated microfluidic channel system that enables controlled tear sample handling and concentration. Together, these modules enhance signal-to-noise ratio and reproducibility, supporting the detection of low-abundance tear biomarkers.

The Raman signal enhancement 402 may include spectral enhancement strategies 406, including optical excitation optimization 404 and AI spectral processing 408. These spectral enhancement strategies 406 can optionally be used with a SERS substrate 410 and/or microfluidic integration 412.

Figure 5:
FIG. 5 illustrates an AI pipeline architecture, showing a preprocessing layer, feature extraction, classifier modules, and a longitudinal monitoring engine.
Figure 5:
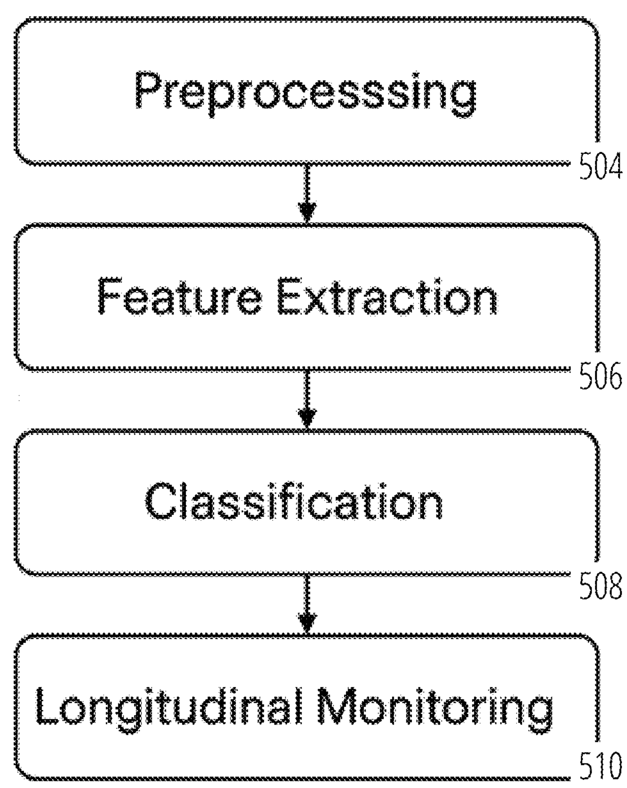

FIG. 5 shows an AI pipeline architecture 502 for Raman-based tear diagnostics. The AI pipeline architecture 502 for Raman-based tear diagnostics is structured to process raw spectral data into clinically meaningful outputs through a sequential, modular design. This AI pipeline architecture 502 enables the Raman spectroscopy system to function not only as a diagnostic tool but also as a monitoring platform that adapts to patient history, improving personalized care and early detection. The AI pipeline architecture 502 includes four primary components: preprocessing 504, feature extraction 506, classification 508, and longitudinal monitoring 510 and decision support.

Preprocessing 504 Layer. Raw Raman spectra may be corrected for background fluorescence, baseline drift, and noise using polynomial fitting and smoothing algorithms. This layer ensures that spectral artifacts and signal variability, often due to tear film heterogeneity or collection substrate, are minimized prior to analysis.

Feature extraction 506 Layer. Once the data are cleaned, the pipeline may apply signal decomposition techniques such as principal component analysis (PCA), wavelet transforms, or neural embedding to identify relevant spectral features. These features may correspond to specific biochemical vibrational modes associated with tear biomarkers like lactoferrin, glucose, or MDA. AI algorithms also extract peak intensity ratios, spectral slope, and composite biomarker signatures. Biochemical peaks of interest (e.g., lipids, cytokines, mucins) are identified using automated peak detection and spectral windowing. Derived features may include peak intensity ratios, bandwidth, and area-under-curve metrics.

Classification 508 Module. Extracted features may be processed using supervised machine learning models such as convolutional neural networks (CNNs), support vector machines (SVMs), or random forest classifiers trained on labeled spectral datasets. These models classify disease states, such as evaporative dry eye, aqueous-deficient dry eye, tumor presence, or inflammatory response. This module assigns diagnostic categories such as "normal," "dry eye," "diabetic profile," or "oxidative stress" based on learned patterns. It can also stratify disease severity or flag anomalous spectra for clinician review.

Longitudinal monitoring 510 and Decision Support. The final layer may integrate current results with prior patient data using a longitudinal tracking engine. This module compares spectral trends over time, detects early deviations from baseline, and generates alerts or treatment suggestions. The AI-enhanced Raman spectroscopy tear analysis system 202 can visualize changes in spectral signatures and provide context-aware decision support for clinicians, enhancing both diagnostic accuracy and ongoing disease management.

Figure 6:
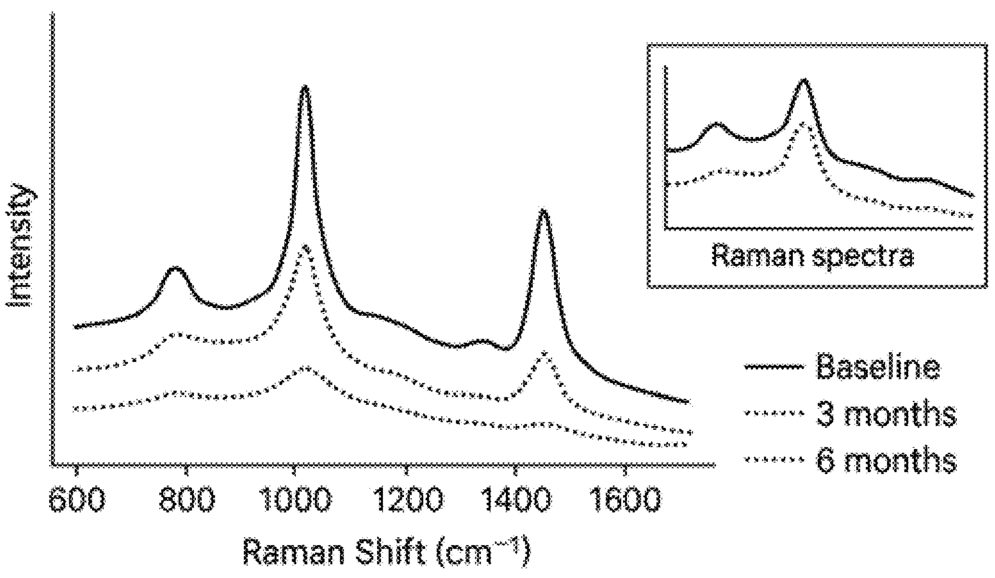
FIG. 6 shows a longitudinal trend monitoring interface with visual comparison of Raman spectra over time for a representative patient.

FIG. 6 illustrates a scenario for a patient 212, showing the longitudinal monitoring of tear biomarkers in a patient 212 with dry eye disease and cataracts.

A 56-year-old female patient presents with symptoms of moderate dry eye disease (DED), including ocular discomfort and visual fluctuation. Clinical evaluation also reveals significant bilateral cataracts, contributing to reduced visual acuity, especially for night driving. The ophthalmologist explains that although cataract surgery will ultimately be needed, precise preoperative measurements, such as keratometry and intraocular lens (IOL) calculations, are unreliable when the ocular surface is compromised by dry eye.

As a result, the ophthalmologist recommends targeted treatment of dry eye disease, guided by AI-Enhanced Raman spectroscopy of the patient's tear film. A treatment plan involving anti-inflammatory drops and ocular surface optimization is initiated, with Raman spectra captured at baseline (Day 0) and follow-up intervals at Day 14 and Day 28 to assess response.

FIG. 6 presents the longitudinal Raman spectral interface, displaying overlaid spectra at three timepoints: baseline (Day 0), follow-up (Day 14), and reassessment (Day 28). Key biomarker peaks, corresponding to lactoferrin (lacrimal function), MMP-9 (inflammation), and malondialdehyde (oxidative stress), are tracked across the time series.

- At baseline, Raman spectra reveal elevated MMP-9 and malondialdehyde levels with suppressed lactoferrin, indicating active inflammation and oxidative stress consistent with moderate DED.
- By Day 14, a reduction in inflammatory markers and increased lactoferrin signal is observed, reflecting early therapeutic response.
- At Day 28, spectral normalization is evident, suggesting restored tear film homeostasis and readiness for cataract biometry.

The ophthalmologist uses these objective molecular trends, alongside clinical examination, to confirm that the ocular surface has stabilized. Cataract surgery planning is resumed, and accurate biometry is performed to determine the optimal intraocular lens (IOL) implant.

This scenario highlights how AI-enhanced Raman tear diagnostics can be integrated into the surgical planning workflow, ensuring that ocular surface optimization precedes intraocular measurements. This approach improves postoperative visual outcomes and exemplifies the value of longitudinal molecular tracking in routine ophthalmic care.

AI-Enhancement of Raman Spectroscopy Analysis of Tears

Artificial Intelligence (AI) significantly enhances the analysis of human tears using Raman spectroscopy by improving accuracy, speed, interpretation, and clinical relevance. Raman spectroscopy provides molecular fingerprints of tear fluid by identifying vibrational energy shifts unique to specific biochemical constituents. When applied to tears, it can detect and quantify a variety of relevant biomarkers, including lipids, inflammatory cytokines, proteins, mucins, and osmolarity-associated metabolites. The surface-enhanced Raman format (SERS) allows for amplification of these signals from microliter-scale samples, making it ideal for non-invasive tear collection.

AI plays a pivotal role in maximizing the clinical value of this molecular data. It enables precise segmentation of spectral features, reduction of noise, real-time classification of disease subtype, and generation of personalized treatment recommendations. Unlike conventional DED diagnostics, the AI-enhanced Raman spectroscopy tear analysis system 202 interprets subtle biomarker variations that may not be detectable through standard visual inspection or mechanical measurements. Moreover, the technology can be used repeatedly to track disease evolution and therapeutic response with high reproducibility.

The integration of AI with Raman spectroscopy facilitates more precise subtyping of DED by biochemically distinguishing between evaporative, aqueous-deficient, and inflammatory variants of dry eye. Using tear biomarker profiling, such as detection of wax esters, MUC5AC mucins, lactoferrin, lysozyme, and cytokines like IL-1β and TNF-α, the AI-enhanced Raman spectroscopy tear analysis system 202 supports personalized diagnosis that replaces trial-and-error strategies with targeted therapy. Early disease signatures, even at subclinical levels, can be identified and used to flag patients before structural damage occurs.

Furthermore, AI models integrated into the platform enhance clinical decision-making by identifying patterns in spectral data, predicting flare-ups, and stratifying patient risk profiles. This computational layer transforms Raman data into usable insights at the point of care, streamlining workflows and improving treatment consistency.

The described AI-enhanced Raman spectroscopy tear analysis system 202 reduces reliance on contact-based and operator-dependent diagnostic methods by providing an alternative approach that enables rapid, non-invasive spectral assessment of tear film biochemistry. Its configuration supports chairside use in routine clinical settings and may be applicable in population screening workflows. The AI-enhanced Raman spectroscopy tear analysis system 202 is particularly relevant for high-risk cohorts, such as post-menopausal individuals, contact lens users, patients undergoing chemotherapy, and those with autoimmune conditions. Accordingly, the AI-enhanced Raman platform may serve as a complementary tool for the evaluation and longitudinal management of dry eye disease.

TABLE 1

ENHANCEMENTS OF RAMAN SPECTROSCOPY FOR TEAR ANALYSIS THROUGH ARTIFICIAL INTELLIGENCE

| AI-Enhanced Functionality | Diagnostic Challenge Addressed | AI Methodology | Clinical Benefit |
|---|---|---|---|
| 1. Noise Reduction and Signal Enhancement | Raman spectra from tears are complex and often noisy due to low analyte concentrations. | Deep learning algorithms such as convolutional neural networks filter baseline drift and denoise spectra while preserving biochemical information. | More reliable detection of weak biomarker signals. |
| 2. Feature Extraction and Pattern Recognition | Key biochemical signatures may be subtle and embedded overlapping peaks. | AI identifies signature spectral peaks for inlipids, proteins, cytokines, mucins; clustering (PCA, t-SNE) and classification (SVM, RF). | Accurate and automatic disease subtyping (e.g., evaporative vs. inflammatory dry eye). |

TABLE 1-continued

ENHANCEMENTS OF RAMAN SPECTROSCOPY FOR TEAR ANALYSIS THROUGH ARTIFICIAL INTELLIGENCE

| AI-Enhanced Functionality | Diagnostic Challenge Addressed | AI Methodology | Clinical Benefit |
|---|---|---|---|
| 3. Clinical Decision Support | Clinicians lack tools to connect Raman spectra with treatment strategies. | AI integrates spectral and clinical data to predict severity, progression, and guide treatment choices. | Enables personalized, evidence-based therapy for each patient. |
| 4. Longitudinal Monitoring and Trend Analysis | Monitoring disease course and treatment response is limited. | AI analyzes spectra over time to track response, forecast flare-ups, and adjust therapy. | Improves chronic management and early detection of relapse. |
| 5. Large-Scale Screening and Population Health | Need for efficient, scalable diagnostics in large populations. | AI automates classification in research and public health settings. | Supports screening of high-risk or underserved populations. |
| 6. Discovery of Novel Biomarkers | Identifying new tear-based biomarkers is challenging. | Deep learning models find hidden molecular patterns and propose new diagnostic candidates. | Advances tearomics and expands non-invasive diagnostic capabilities. |

To improve the sensitivity and reliability of Raman-based tear diagnostics, several signal enhancement techniques may be incorporated into the AI-enhanced Raman spectroscopy tear analysis system 202. These methods optimize photon interaction with low-volume tear film samples and are compatible with both non-contact and cartridge-based collection modes. Table 2 summarizes these techniques and their applicability to tear film analysis:

TABLE 2

Signal Enhancement Techniques for Raman Spectroscopy of Tears

| Technique | Description |
|---|---|
| Near-Infrared (NIR) Excitation | Uses 785 nm, 830 nm, or 1064 nm lasers to reduce autofluorescence from the ocular surface, improving signal clarity for tear constituents. |
| Resonance Raman Spectroscopy (RRS) | Laser excitation is tuned to match absorption bands of specific tear biomarkers, selectively enhancing Raman signal from low-abundance molecules such as cytokines and AGEs. |
| Confocal Raman Spectroscopy (CRS) | Employs a confocal optical path with a pinhole to reject out-of-focus light, enabling precise sampling of the tear meniscus or localized ocular surface regions. |
| Enhanced Collection Optics | Utilizes fiber-coupled optics, aspheric lenses, or GRIN lenses to maximize light collection from the tear film, especially in low-volume or evaporated states. |
| Time-Gated Raman Spectroscopy | Applies pulsed lasers and fast-gated detectors to distinguish weak Raman signals from background fluorescence in tear proteins and lipids. |
| Optical Clearing Agents (OCAs) | Though less common in tear analysis, biocompatible agents may hypothetically reduce surface scattering for improved Raman interrogation of thickened or opaque tear films. |

TABLE 2-continued

Signal Enhancement Techniques for Raman Spectroscopy of Tears

| Technique | Description |
|---|---|
| Swept Source Raman Spectroscopy (SSRS) | Utilizes tunable excitation or detection wavelengths to dynamically scan across Raman bands. Enhances spectral resolution, biomarker targeting, and AI adaptability for fluctuating tear film compositions. |

These enhancements allow for robust detection of diagnostically significant molecules, including protein aggregates, inflammatory cytokines, and oxidative stress markers, using minute volumes of tear fluid. Their integration into the modular platform enables adaptive deployment based on sample characteristics, target biomarker class, and required diagnostic depth.

Key Embodiments for Raman Signal Enhancement

TABLE 3

Benefits of Confocal Raman Spectroscopy in Tear Diagnostics

| Benefit | Description | Diagnostic Relevance |
|---|---|---|
| Improved Signal Collection | Pinhole-based rejection of out-of-focus light | Enhances SNR for dilute biomarkers in tear film or substrates |
| Enhanced Depth Profiling | Layer-specific signal capture via adjustable focal plane | Enables analysis across lipid, aqueous, and mucin layers or strip gradients |
| Reduced Background Noise | Filters out interference from ocular surface or collection device surfaces | Provides cleaner input for AI-based classification models |
| High Spatial Resolution | Localized scanning of tear meniscus or substrate regions | Identifies areas of high biomarker concentration or tear film heterogeneity |

TABLE 3-continued

Benefits of Confocal Raman Spectroscopy in Tear Diagnostics

| Benefit | Description | Diagnostic Relevance |
|---|---|---|
| Molecular Selectivity | Focused detection improves resolution of overlapping spectral peaks | Distinguishes similar molecules like albumin vs. lactoferrin |
| Compatibility with Enhancements | Supports integration with NIR lasers, SERS, or clearing agents | Expands diagnostic versatility and depth reach in compact systems |

Confocal Raman Spectroscopy (CRS) enhances the resolution and diagnostic utility of Raman-based tear analysis by selectively capturing photons from a narrowly defined focal plane, thereby eliminating out-of-focus and scattered light. When applied to tear film scanning or analysis of tear-soaked substrates (e.g., Schirmer strips or hydrogel pads), CRS dramatically improves signal-to-noise ratio (SNR) and enables spatial targeting of molecular features. This allows for high-precision detection of low-abundance analytes such as cytokines, lipids, and oxidative stress markers. CRS also enables depth-resolved spectral profiling in layered or stratified tear films, supporting longitudinal monitoring or differentiation between reflex and basal tear components.

A major benefit of CRS in tear diagnostics is its ability to significantly improve the signal-to-noise ratio (SNR), especially when detecting low-abundance biomarkers. Tear film and tear collection media often exhibit substantial optical background due to substrate variability, surface glare, or fluorescence from surrounding tissues. CRS suppresses these unwanted signals, isolating Raman-scattered photons from the intended focal plane and yielding cleaner, higher-quality spectra.

CRS also enables high spatial resolution, which is particularly advantageous when performing Raman scans over small tear reservoirs, specific segments of the ocular surface, or different zones of a collection strip. This allows clinicians and researchers to localize regions with higher molecular concentration, such as cytokine-rich tear menisci or drug-metabolite accumulation zones, enabling more precise biochemical characterization.

Moreover, CRS supports depth profiling. By incrementally adjusting the focal depth within a tear-absorbing matrix or across a stratified tear layer, it is possible to capture Raman spectra from different tear phases (e.g., lipid, aqueous, mucin) or layers within a porous substrate. This depth-resolved data improves understanding of biomarker partitioning and may reveal longitudinal shifts in disease-related molecules over the course of treatment or diurnal variation.

CRS also reduces background noise from adjacent optical structures such as the cornea, eyelashes, or collection device materials. In AI-Enhanced systems, this cleaner signal improves model input fidelity, enabling higher classification accuracy for disease states such as dry eye disease, diabetes, or inflammatory conditions.

Finally, CRS enhances molecular selectivity. The narrow confocal volume increases the ability to distinguish among overlapping biomolecular signals in Raman spectra. This allows for more precise targeting of diagnostically relevant species such as MMP-9, interleukins, or stress-induced proteins. When used in conjunction with AI algorithms, CRS-generated spectral data improves classification, monitoring, and therapeutic decision-making in tear-based diagnostics.

TABLE 4

Integration of Swept Source Raman Spectroscopy within Modular Architecture

| Module | Swept Source Enhancement |
|---|---|
| Excitation Module | Tunable laser source with wavelength sweeping capability for resonance optimization |
| Detection Module | Variable grating or filter array for dynamic detection band selection |
| AI Interpretation Unit | Receives sequential spectral frames and integrates swept bands into classification workflow |
| Control Interface | Operator or AI-directed control over sweep parameters, resolution, and activation thresholds |
| Display Module | Visualizes multi-frame output or composite spectral map |
| Power/Data Unit | Adjusted power management and memory buffer to support high-speed spectral acquisition |

The inclusion of swept source Raman functionality broadens the diagnostic precision and adaptability of the AI-enhanced Raman spectroscopy tear analysis system 202, supporting a range of patient scenarios and improving biomarker detection under variable physiologic and environmental conditions.

The AI-enhanced Raman spectroscopy tear analysis system 202 may further include a swept source Raman spectroscopy (SSRS) configuration as an optional or preferred embodiment. Swept source Raman spectroscopy utilizes tunable excitation or detection wavelengths to acquire multiple spectral bands in rapid succession. This approach provides enhanced flexibility in biomarker targeting, signal optimization, and adaptive analysis workflows.

In a swept source configuration, the excitation module is equipped with a laser 804 source capable of dynamic wavelength modulation across a designated range. Alternatively, the detection system may feature tunable filters or gratings that scan across the Raman shift axis. These features allow the AI-enhanced Raman spectroscopy tear analysis system 202 to focus spectral interrogation on user-defined or AI-determined regions of interest, enhancing signal detection for biomarkers of interest while avoiding spectral regions with high noise or irrelevant data.

This capability is particularly valuable in the analysis of tear film, where small sample volumes and fluctuating compositions may otherwise limit the ability to resolve weak or overlapping Raman signatures. By sweeping the excitation or detection range, the AI-enhanced Raman spectroscopy tear analysis system 202 can isolate spectral windows that maximize contrast between disease and non-disease states or between different physiological phases.

The SSRS embodiment integrates seamlessly into the system's modular architecture. A swept-source laser unit may be included as a field-upgradable component in the excitation module, while tunable detection optics may be linked via plug-and-play interface to the spectral analysis subsystem. The AI interpretation engine is configured to receive and process sequentially acquired spectral frames, enabling real-time reconstruction and classification of enriched spectra.

Use cases for SSRS within this AI-enhanced Raman spectroscopy tear analysis system 202 include:

Enhanced profiling of tear glucose, protein glycation, and AGE accumulation in diabetic patients Adaptive resonance matching in inflammatory tear profiles (e.g., IL-1β, TNF-α)

Dynamic optimization for ocular surface stress markers under fluctuating lighting or blink patterns Real-time wavelength scanning in point-of-care or telehealth deployments where a single optimal excitation wavelength may not be pre-determined Swept source functionality may be activated based on operator input, AI-driven spectral analysis needs, or diagnostic protocol settings. AI models may recommend sweeping only in cases where static analysis yields ambiguous classification, thereby conserving energy and computational resources.

Resonance-Enhanced Raman Spectroscopy for Biomarker Amplification

TABLE 5

Benefits of Resonance Raman Spectroscopy (RRS) in Tear Diagnostics

| Benefit | Description |
| --- | --- |
| Increased Sensitivity for Low-Abundance Biomarkers | RRS can detect molecules that are otherwise too dilute to be identified reliably in basal tears—e.g. cytokines, oxidative stress markers, or neuropeptides. |
| Enhanced Signal-to-Noise Ratio | Improves the diagnostic value of Raman data in noisy conditions or small sample volumes, which is ideal for non-contact ocular surface scanning. |
| Molecular Selectivity | Allows AI models to differentiate between structurally similar biomolecules with overlapping spectral features (e.g., albumin vs. globulin proteins). |
| Compatibility with AI-Driven Spectral Interpretation | RRS-enhanced spectra provide sharper, more distinctive peaks for AI feature extraction and classification, which improves model accuracy. |
| Enables Compact, Low-Power Systems | With stronger signals, you may be able to use lower-power lasers, expanding portable or telehealth-optimized designs. |

The AI-enhanced Raman spectroscopy tear analysis system 202 may optionally incorporate resonance-enhanced Raman spectroscopy (RERS), also referred to as Resonance Raman Spectroscopy (RRS), as a signal optimization feature in select embodiments.

This variation is particularly valuable when targeting specific biomolecules that exhibit characteristic electronic absorption bands. In such cases, the excitation wavelength of the Raman source is tuned to closely match the electronic transition of the molecule of interest. The signal enhancement can be $10^3$ to $10^6$ times greater than conventional Raman signals, especially useful for trace biomolecule detection in tears.

This enhancement mechanism is achieved without the use of external labels or dyes and relies instead on intrinsic molecular properties. The resonant excitation selectively amplifies Raman scattering from the target molecule while leaving background signals relatively unchanged, significantly improving the signal-to-noise ratio. In the context of tear analysis, this approach is well suited for detecting trace concentrations of diagnostically significant biomarkers such as:

Oxidative stress markers (e.g., nitric oxide derivatives, lipid peroxidation products)

Inflammatory cytokines with conjugated aromatic structures (e.g., IL-6, TNF-α)

Aromatic amino acids or protein structures prone to conformational change (e.g., neurodegenerative disease markers)

Glycation end-products and metabolic byproducts in diabetic patients

The application of RERS is compatible with the modular system architecture described elsewhere in this specification. A resonance-enabled embodiment may feature a tunable or wavelength-selectable laser 804 source integrated into the Raman excitation module, either as a factory-set component or as a field-swappable unit. Optical filters and detection electronics may be configured to accommodate the adjusted spectral characteristics resulting from resonant enhancement.

From a clinical utility perspective, the use of RERS permits detection of otherwise sub-threshold biomarker levels without increasing power output or exposure time. This is particularly advantageous in non-contact ocular scanning, where minimizing tissue exposure is desirable. The improved detection fidelity also enhances the precision of AI-based classification algorithms by providing sharper spectral peaks for feature extraction and classification.

The resonance-based configuration may be specified as a preferred embodiment when operating in disease-specific diagnostic modes, such as detecting early-stage diabetic microvascular changes, oxidative stress in neurodegeneration, or low-abundance pharmacologic metabolites. The resonance-enabled module may be software-controlled to activate only under conditions where resonance is expected to improve accuracy.

This enhancement does not alter the overall system workflow or AI interpretation framework but adds diagnostic sensitivity and biochemical selectivity where standard Raman configurations may be insufficient.

TABLE 6

Benefits of Resonance Raman Spectroscopy (RRS) in Tear Diagnostics

| Benefit | Description |
| --- | --- |
| Increased Sensitivity for Low-Abundance Biomarkers | RRS can detect molecules that are otherwise too dilute to be identified reliably in basal tears—e.g. cytokines, oxidative stress markers, or neuropeptides. |
| Enhanced Signal-to-Noise Ratio | Improves the diagnostic value of Raman data in noisy conditions or small sample volumes, which is ideal for non-contact ocular surface scanning. |
| Molecular Selectivity | Allows AI models to differentiate between structurally similar biomolecules with overlapping spectral features (e.g., albumin vs. globulin proteins). |
| Compatibility with AI-Driven Spectral Interpretation | RRS-enhanced spectra provide sharper, more distinctive peaks for AI feature extraction and classification, which improves model accuracy. |
| Enables Compact, Low-Power Systems | With stronger signals, you may be able to use lower-power lasers, expanding portable or telehealth-optimized designs. |

Table 6 highlights the functional advantages of integrating RRS into the disclosed tear analysis system, particularly when applied to embodiments involving handheld probes, slit-lamp-mounted devices, or non-contact ocular surface scanners. RRS enhances sensitivity, selectivity, and signal quality, enabling reliable detection of low-abundance biomarkers while supporting compact, AI-compatible, and energy-efficient designs ideal for clinical or remote applications.

Tear Sampling

TABLE 7

| Biomolecular Composition of Normal Human Tears | | | |
|---|---|---|---|
| Biomarker | Anatomic Source | Relative Quantity | Representative Raman Shift ($cm^{-1}$) |
| Lactoferrin | Lacrimal gland | High | 620-650 |
| Lysozyme | Lacrimal gland | High | 990-1005 |
| Lipocalin-1 | Lacrimal gland | Medium | 1445-1465 |
| Albumin | Plasma leakage/ interstitial fluid | Low | 1550-1580 |
| MUC5AC (mucin) | Goblet cells of conjunctiva | Medium | 1200-1250 |
| Immunoglobulin A (IgA) | Lacrimal gland/ conjunctival plasma cells | Medium | 830-870 |
| Electrolytes (Na+, Cl−) | Aqueous layer, systemically derived | High | Broad band 200-400 |
| Lipids (e.g., cholesterol ester) | Meibomian glands | Medium | 1430-1470 |
| Urea | Plasma-derived | Low | 1000-1050 |
| Glucose | Systemic circulation | Low | 1080-1120 |

Tear fluid is a complex, multilayered biofluid composed of molecules secreted from various ocular and systemic sources. It reflects both local ocular surface homeostasis and systemic physiological status, making it an ideal non-invasive medium for molecular diagnostics. Raman spectroscopy, with its sensitivity to vibrational signatures of biochemical bonds, enables precise detection of these constituents based on their unique spectral fingerprints.

Table 7 summarizes key biomarkers commonly found in normal human tears, including their anatomic origin, relative abundance, and representative Raman shift ranges. These data support spectral targeting during tear analysis and enhance the interpretive power of AI-enhanced Raman spectroscopy tear analysis systems 202.

Lactoferrin and lysozyme, both secreted by the lacrimal gland, are among the most abundant tear proteins and exhibit strong Raman signatures between 620-650 $cm^{-1}$ and 990-1005 $cm^{-1}$, respectively. Their concentrations are useful markers of lacrimal gland function and ocular surface immune defense.

Lipocalin-1, also derived from the lacrimal gland, appears in moderate concentrations and contributes to lipid binding and tear film stability. It shows Raman activity in the 1445-1465 $cm^{-1}$ region, overlapping with lipid-associated modes.

Albumin and urea, detected at low levels, typically enter the tear film via passive diffusion from plasma or interstitial fluid. Albumin appears near 1550-1580 $cm^{-1}$, while urea shows a signature between 1000-1050 $cm^{-1}$, providing insight into systemic permeability and metabolic state.

MUC5AC, a high-molecular-weight mucin secreted by conjunctival goblet cells, shows medium abundance and a broad Raman signal around 1200-1250 $cm^{-1}$, reflecting its glycoprotein composition and relevance to tear film mucous layer integrity.

Immunoglobulin A (IgA), produced by conjunctival plasma cells and the lacrimal apparatus, plays a critical immunoprotective role. It is typically observed in the 830-870 $cm^{-1}$ spectral region.

Electrolytes, including sodium and chloride ions, contribute to tear osmolarity and exhibit broad Raman activity in the 200-400 $cm^{-1}$ range. These systemic markers offer insight into hydration and osmotic stress.

Lipids, particularly cholesterol esters from the Meibomian glands, support tear film stability and lipid layer formation. Their Raman peaks typically fall within the 1430-1470 cm region.

Glucose, though present in low concentration in healthy individuals, appears between 1080-1120 $cm^{-1}$. Elevations in glucose may signal systemic metabolic conditions such as diabetes mellitus.

This biomarker catalog supports targeted Raman interrogation and enables personalized, AI-Enhanced interpretation of tear-based spectra for clinical and diagnostic applications.

TABLE 8

| Options for Tear Sampling | | | | |
|---|---|---|---|---|
| Method | Description | Benefits | Limitations | Patent Suitability |
| Direct In Situ Contactless Analysis | Raman probe is focused directly on the tear film without physical contact | Non-invasive, minimal risk, fast | Requires patient cooperation and optical stabilization | High-contactless optical head |
| Microcapillary Tube Collection | Tear fluid is collected using microcapillaries for off-site or delayed Raman analysis | Clinically common, standardized volumes | Invasive, requires skilled handling, time-consuming | Moderate-may support modular sample cartridge |
| Schirmer Strip Sampling | Absorbent paper placed in lower eyelid to collect tears, then dried and analyzed | Simple, low-cost | Non-uniform sample, potential for contamination or evaporation artifacts | Moderate-could be referenced in a sample prep module |
| Diagnostic Cartridge with Absorbent Pad | A sterile, disposable cartridge with a tear-wicking membrane placed under probe | Standardized, modular, rapid | Must balance absorbency with Raman compatibility | High |
| Hydrogel Pad or Contact Lens Sampling | Pre-wetted lens or gel pad absorbs tear fluid, then analyzed in probe interface | Conforms to eye shape, enhances reproducibility | Less common, requires contact | Moderate |

Mechanisms of Biomarker Appearance in Tear Film

Tears serve as a non-invasive fluid medium containing a rich repertoire of biomarkers that reflect both local ocular and systemic physiological states. The mechanism by which biomarkers appear in tear film varies by source and disease state. Through the use of Raman spectroscopy and AI-enhanced signal processing, even weak or diluted biomarker signals in tears can be extracted, amplified, and interpreted, offering a powerful, non-invasive approach to ocular diagnostics. The ability to detect oxidative stress, inflammatory markers, or tumor-associated molecules in tears is not only feasible but scientifically grounded in the following integrated physiological, anatomical, and pathological pathways:

Ocular Surface Secretion: Proteins such as lactoferrin, lysozyme, and secretory IgA are produced directly by the lacrimal glands and ocular surface epithelia. Their levels may vary in response to inflammation, infection, or gland dysfunction.

Transudation from Systemic Circulation: Low-molecular-weight analytes, such as glucose and cytokines, may diffuse passively from blood vessels in the conjunctiva or lacrimal gland vasculature into the tear film. This provides a biochemical snapshot of systemic conditions such as diabetes or systemic inflammation.

Stress-Induced Shedding or Leakage: During disease progression or acute stress, the integrity of the ocular surface may become compromised, allowing intracellular or extracellular matrix components to enter the tear film. This includes MMPs, heat shock proteins, and lipid mediators.

Neurogenic and Hormonal Influence: Tear composition may also change in response to neuroendocrine signals, reflecting emotional state, circadian rhythm, or hormonal imbalances. Some biomarkers such as cortisol or neuropeptides can be detected and linked to broader physiological profiles.

Table 9 summarizes biomarkers found or suspected in tear film, categorized by the physiological or pathological pathway of transport, the underlying mechanism, and associated ocular conditions. These relationships form the scientific basis for tear-based molecular diagnostics using Raman spectroscopy and AI analysis.

TABLE 9

Mechanisms of specific biomarker appearance in tear film

| Biomarker | Pathway | Mechanism | Associated Condition(s) |
|---|---|---|---|
| Malondialdehyde (MDA) | Aqueous humor transudation | Passive diffusion across corneal endothelium | Glaucoma, oxidative stress |
| Interleukin-6 (IL-6) | Barrier breakdown | Increased vascular permeability during inflammation | Uveitis, diabetic retinopathy |
| Complement Factor H (CFH) | Paracrine/ neurogenic secretion | Lacrimal or epithelial response to retinal degeneration | AMD |
| Cytochrome c | Conjunctival/ episcleral diffusion | Mitochondrial release and local inflammatory signaling | Intraocular tumors |
| Advanced Glycation End-products (AGEs) | Aqueous humor transudation | Leakage from anterior chamber under metabolic stress | AMD, diabetic eye disease |
| Matrix Metalloproteinase-9 (MMP-9) | Barrier breakdown | Release due to breakdown of blood-ocular barriers | Uveitis, AMD |
| Lactoferrin/ Lysozyme/IgA | Ocular Surface Secretion | Lacrimal gland and epithelial secretion | Dry Eye Disease, Infection, Gland Dysfunction |
| Glucose/ Cytokines | Systemic Circulation Transudation | Passive diffusion from conjunctival vasculature | Diabetes, Systemic Inflammation |
| MMPs/Heat Shock Proteins/Lipids | Stress-Induced Leakage | Cellular breakdown and matrix degradation | Inflammation, Tissue Stress, Degeneration |
| Cortisol/ Neuropeptides | Neurogenic/ Hormonal Influence | Hormonal or neural signal response | Stress, Circadian Dysregulation, Hormonal Imbalance |

Table 9 outlines representative biomarkers that may be detected in tear film, categorized by their physiological or pathological transport pathways, underlying mechanisms of migration, and associated ocular conditions. Each biomarker plays a recognized or emerging role in ocular disease processes, ranging from oxidative stress and inflammation to neovascular and neoplastic transformation. Their presence in tears reflects the dynamic interface between intraocular environments and the ocular surface. By elucidating these pathways, Table 9 supports the rationale for tear-based molecular diagnostics using AI-enhanced Raman spectroscopy, which is uniquely suited to detect and interpret such biomarkers even at low concentrations.

Circadian and Environmental Variability in Tear Biomarkers

Tear biomarkers are dynamic and can fluctuate significantly over the course of a day due to a combination of physiological rhythms, environmental exposures, and behavioral influences. These fluctuations are meaningful to consider when interpreting diagnostic results derived from Raman spectroscopy or traditional immunoassays.

One key factor is the diurnal variation in tear production. Aqueous tear secretion generally peaks in the morning and diminishes throughout the day. As tear volume decreases, biomarkers such as osmolarity, inflammatory cytokines, and stress proteins may become more concentrated. This physiologic variation is further modulated by hormonal influences and circadian regulation of lacrimal gland function.

Reflex tearing, triggered by environmental stimuli such as wind, screen time, or ocular discomfort, can transiently dilute the tear film. This dilution effect reduces the concentration of biomarkers like MMP-9, IL-6, and TNF-$\alpha$, potentially masking the biochemical signature of dry eye or inflammation. Conversely, decreased blinking or tear stagnation can lead to localized accumulation of proinflammatory factors, particularly in patients with a reduced blink rate or poor tear clearance.

Environmental exposure also plays a role. Factors such as low humidity, air pollution, allergen load, or contact lens wear can directly induce inflammatory responses on the ocular surface, resulting in spikes in cytokine levels and oxidative stress markers throughout the day. These changes may occur independent of structural or chronic disease, reflecting acute physiologic reactivity.

Mechanical stress from blinking over a compromised epithelial surface contributes to the release of damage-associated molecules and epithelial stress biomarkers. This mechanism is especially relevant in dry eye patients and often leads to worsening symptoms and elevated biomarker levels later in the day.

Systemic influences also affect tear biomarker profiles. In patients with diabetes, autoimmune disorders, or metabolic syndromes, systemic inflammation and hormonal cycling can modulate tear cytokine concentrations. Glucose and cortisol levels, for instance, may fluctuate diurnally and impact both tear composition and ocular surface health.

Importantly, the immune system itself operates on a circadian schedule. Expression levels of immune-related tear biomarkers, including IL-1β, TNF-α, and HLA-DR, may follow a 24-hour rhythm, influenced by neural and hormonal regulation of immune cells in the conjunctiva and lacrimal tissue.

Finally, tear film instability and dysfunction of the lipid or mucin layers contribute to shifts in tear biomarker concentration over time. As the day progresses, meibomian gland output may decline, leading to tear film breakup and evaporative stress, which in turn alters the biochemical environment at the ocular surface.

In light of this variability, diagnostic interpretation could account for the timing and context of sample collection. AI-enhanced systems can mitigate variability by incorporating temporal metadata, enabling normalization or stratified interpretation of Raman spectral data and biomarker panels.

Understanding and adjusting for tear biomarker fluctuation is meaningful for ensuring reliable diagnostics and optimizing personalized treatment planning.

Role of AI in Managing Fluctuating Tear Biomarkers

The analysis of tear biomarkers is often complicated by natural physiological variation and environmental influences. Artificial Intelligence (AI) can be used as a computational tool to manage this complexity, enabling more consistent interpretation of multivariate biochemical data collected from the ocular surface.

AI algorithms can incorporate temporal factors, such as time of day, to normalize data for diurnal variation in biomarker concentrations. For instance, fluctuations in interleukin-6 (IL-6) or osmolarity throughout the day may be accounted for by referencing learned circadian patterns, reducing the likelihood of misclassification based on sampling time alone.

In addition to temporal normalization, AI platforms can integrate contextual metadata, including ambient environmental conditions (e.g., humidity, temperature, air quality), behavioral data (e.g., screen time duration), and recent clinical interventions (e.g., administration of lubricants or anti-inflammatory drops). These variables provide additional explanatory value and support more contextually appropriate interpretation of biomarker levels.

AI also facilitates multivariate pattern recognition, allowing for the identification of clinically relevant biomarker combinations that may not be informative when considered individually. For example, concurrent changes in MMP-9, lipid degradation patterns, and tear osmolarity may collectively suggest an inflammatory exacerbation, even if each parameter alone falls within its respective reference range.

For patients undergoing serial monitoring, AI-based tools can apply trend analysis and smoothing algorithms to distinguish sustained shifts or acute deviations from background variability. This supports early recognition of therapeutic response, disease progression, or loss of disease control.

Some AI models are capable of adaptive learning, allowing the AI-enhanced Raman spectroscopy tear analysis system 202 to establish individualized baselines based on a patient's unique biomarker profile and fluctuation patterns. This personalization may enhance the detection of significant deviation, even when values remain within population-based normative thresholds.

Finally, AI can support longitudinal treatment evaluation by comparing molecular response trends over time and correlating these with prior therapeutic interventions. This functionality may aid clinicians in decisions regarding treatment escalation, tapering, or maintenance strategies based on molecular evidence rather than solely clinical symptoms or exam findings.

Taken together, AI can provide a computational framework for interpreting tear biomarker data with greater consistency and contextual sensitivity. Its ability to synthesize temporal, environmental, and patient-specific data supports a more robust assessment of ocular surface health over time.

AI-Enhancement of Ramon Spectroscopy and Tear Diagnostics

Figure 7:
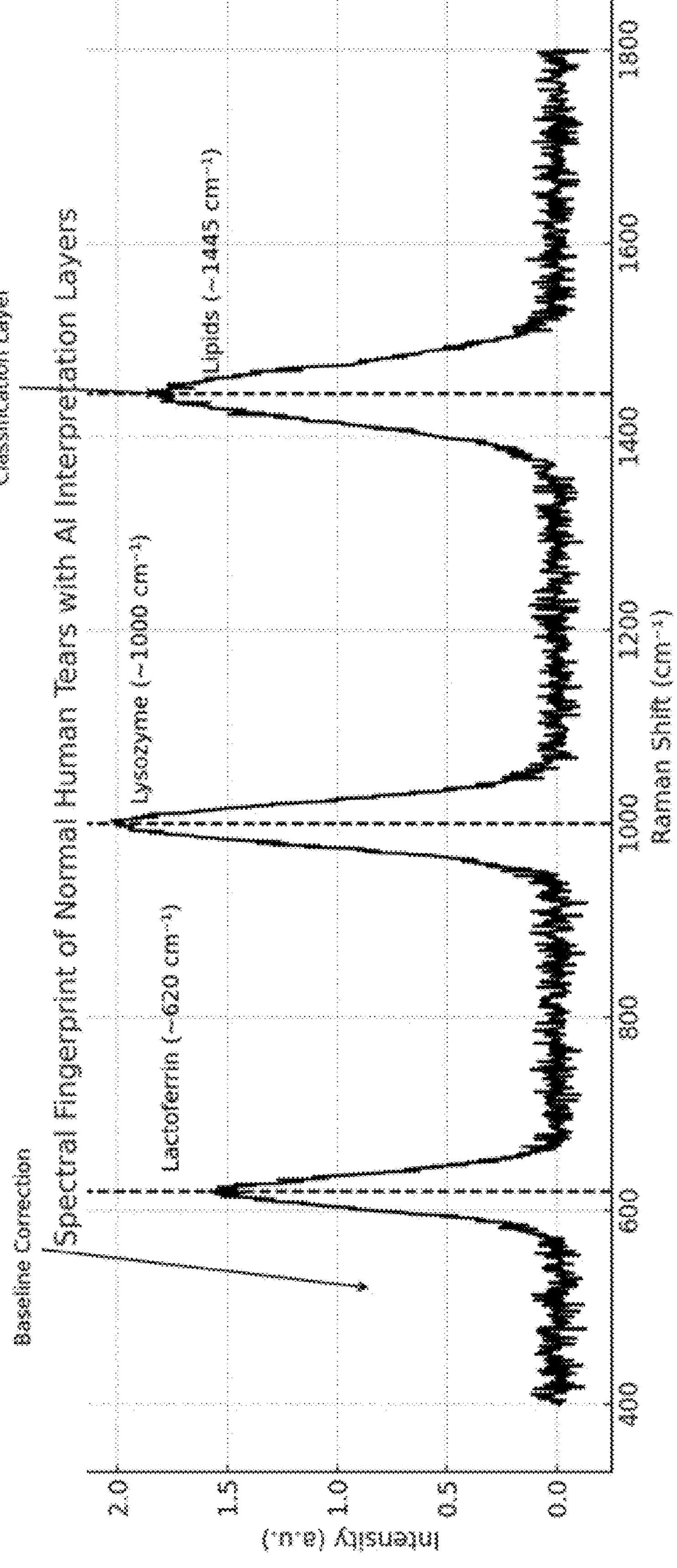
FIG. 7 shows a spectral fingerprint output with AI interpretation layers.

FIG. 7 represents a typical Raman spectral fingerprint of normal human tears, illustrating the layered steps of AI interpretation. The spectral curve includes a 'baseline', the underlying signal drift or fluorescence that can obscure true spectral features. Baseline correction is a preprocessing step that mathematically flattens or removes this component, enabling clearer identification of meaningful peaks.

Automated peak detection follows baseline correction and scans the spectrum for local maxima within diagnostically relevant regions. These include known biochemical markers such as lactoferrin near 620 $cm^{-1}$, lysozyme around 1000 $cm^{-1}$, and lipid bands near 1445 $cm^{-1}$. These peaks are highlighted as representative features in a normal tear film profile.

All identified spectral features are input into a classifier module. The classifier is an AI component trained using machine learning models to recognize diagnostic patterns across multiple regions of the spectrum simultaneously. Rather than focusing on a single biomarker, the classifier analyzes the full fingerprint to determine clinical categories such as normal, dry eye, or diabetes. It does so through probability-weighted comparisons with annotated spectral databases. This multivariate, probabilistic interpretation results in a clinically meaningful diagnosis based on the total biochemical signature contained within the tear film.

Figure 8:
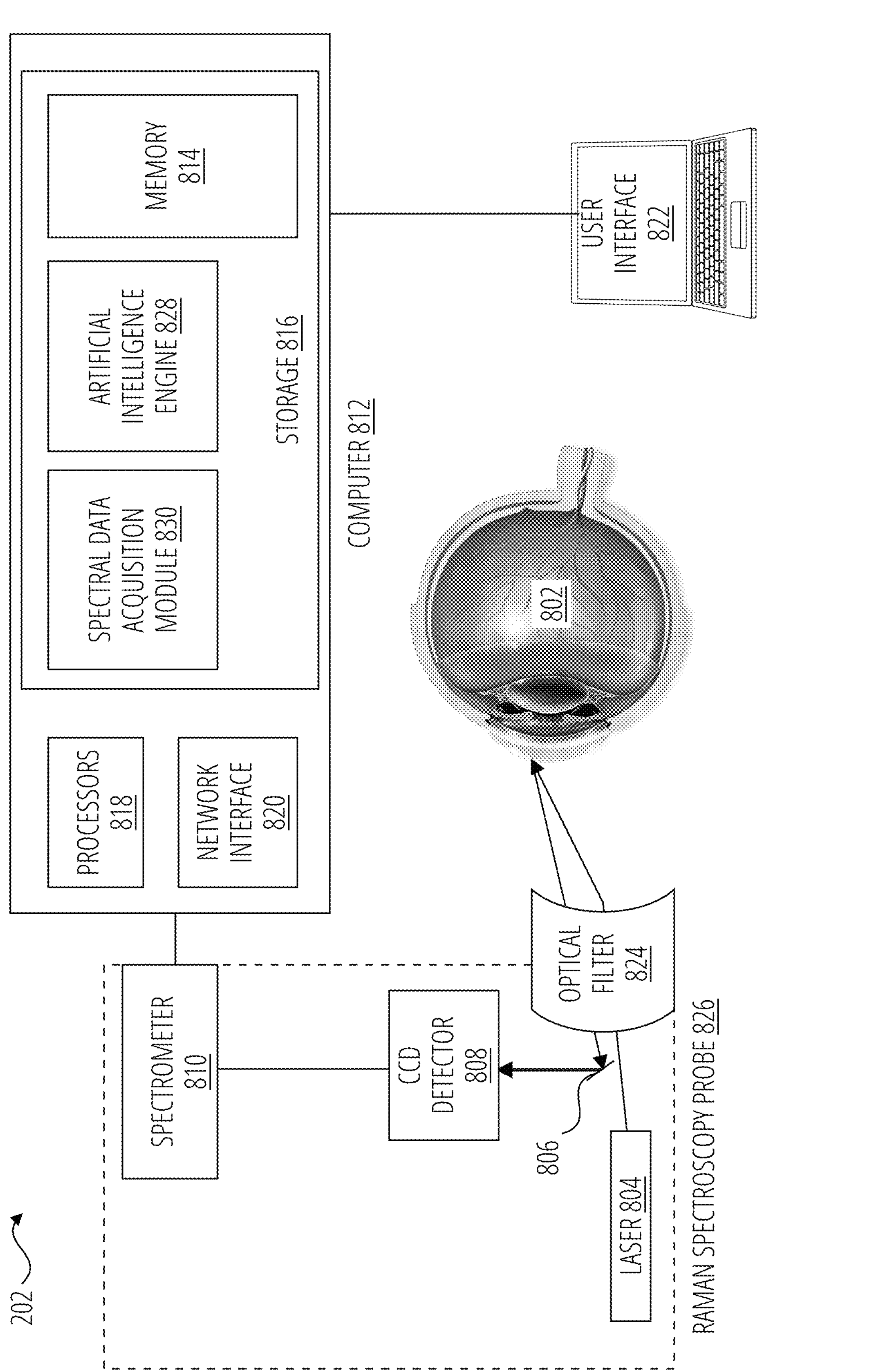
FIG. 8 depicts a representative system architecture of the AI-enhanced Raman spectroscopy tear analysis system.

FIG. 8 depicts a representative system architecture of the AI-enhanced Raman spectroscopy tear analysis system 202. In this figure, a laser 804, such as a monochromatic excitation laser, is directed onto tear film on the eye 802 surface. In some embodiments, the tears may be removed from the eye 802 (perhaps placed in glassware or a slide) and analyzed with the AI-enhanced Raman spectroscopy diagnostic AI-enhanced Raman spectroscopy tear analysis system 202 separately from the eye 802. The interaction between the laser 804 and tear film generates Raman-scattered light, which returns along the same optical path. A beam splitter 806 is positioned to intercept the backscattered light and redirect the Raman-scattered photons into a charge-coupled device 808 while allowing the laser light to pass onto the eye 802 surface. The spectrometer 810, which receives data from the charge-coupled device 808, receives and processes the scattered light into digital spectral data. This data is then transmitted to computer 812, where spectral features are analyzed using an artificial intelligence engine 828. Diagnostic insights, including biomarker identification and classification of a diagnosis, are output through a user interface 822 (on the display screen 210 in some embodiments) for clinical interpretation. FIG. 8 also highlights the seamless flow of optical and digital signals from excitation to diagnosis, demonstrating how signal integrity and clinical feedback are preserved through each stage of the AI-enhanced Raman spectroscopy tear analysis system 202.

In some embodiments, the laser 804, the beam splitter 806, the charge-coupled device 808, and the spectrometer 810 may be integrated into a handheld Raman spectroscopy probe 826. The Raman spectroscopy probe 826 may be mounted on a standard ophthalmic slit lamp 204, which stabilizes both the Raman spectroscopy probe 826 and the patient's eye 802 during examination. The probe optics include the laser 804 with a focusing lens assembly and an optical filter 824 for rejecting Rayleigh scattered light while capturing inelastic Raman scatter.

In the process shown in FIG. 8, the laser 804 is directed onto the tear film of the eye 802 through a shared optical system that includes video transmission capability. Raman-scattered light reflected from the tear film and returns along the same optical path. The returning light is diverted by a beam splitter 806 toward a charge-coupled device 808, which converts the scattered light into raw spectral data. A Raman spectrometer 810 uses diffraction gratings to disperse the light and measure Raman shifts corresponding to molecular vibrations. The spectrometer 810 sends spectral data in digital format to the computer 812, where the one or more processors 818 use the artificial intelligence engine 828, which analyzes the spectral signature to detect molecular features indicative of glucose, protein, malondialdehyda, or lipid content-biomarkers associated with dry eye, diabetes, pharmacologic exposure, etc. The artificial intelligence engine 828 interprets the data and transmits the diagnostic output (including classification results, molecular probabilities, and other indicators) to a user interface 822 for clinical review.

The computer 812 may have one or more processors 818 communicatively connected to one or more network interfaces 820 and one or more storage 816 devices. The storage 816 may include memory 814, such as random access memory, read-only memory, and similar types of volatile or non-volatile memory devices. Storage 816 may also include longer-term storage 916 devices such as optical storage, disk drives, solid-state drives, and similar. The storage 816 may include non-transitory instructions for the processors 818, one or more spectral data acquisition modules 830, and one or more artificial intelligence engines 828. The computer 812 may be communicatively connected to one or more user interfaces 822, such as a display screen 210, a keyboard, a touchscreen, a mouse, a laptop, a tablet, a smartphone, a smart watch, another computer, or a similar device. The connection between the computer 812 and the user interface 822 may be through the network interface 820 to a network, or the connection may be through wires or wireless. The network interface 820 may be operatively coupled to the Internet and/or to a cloud-based computing environment.

Note that some (or all) of the functionality shown here in the computer 812 could be incorporated in the spectrometer 810.

The system's artificial intelligence component is trained on centrally acquired spectral datasets to identify and classify disease-relevant molecular patterns, even at diluted concentrations. This central acquisition strategy reduces anatomical variability, enhances reproducibility, and enables rapid, patient-friendly diagnostic screening of soluble biomarkers associated with dry eye, diabetes, pharmacologic exposure, etc.

In certain embodiments, the disclosed AI-enhanced Raman spectroscopy tear analysis system 202 enhances diagnostic reliability by employing temporal averaging, time-aware normalization, and anatomical inference based on spectral features. During a single scan session, multiple Raman spectra may be acquired and averaged to minimize stochastic noise and improve signal fidelity. This approach increases the robustness of spectral classification, particularly in the presence of ambient lighting variability or minor ocular motion.

To address potential variability due to diurnal biomarker fluctuation, the AI-enhanced Raman spectroscopy tear analysis system 202 includes time-of-day normalization strategies based on known circadian expression patterns of tear film biomarkers. This normalization allows for the consistent interpretation of measurements collected at different times.

Additionally, the AI/ML interpretation model 924 is trained to infer the approximate anatomical origin of a given spectrum-central vs. peripheral-based on signal shape, intensity, and feature distribution, even in the absence of explicit Raman spectroscopy probe 826 position metadata. This inferred location informs a context-adjusted confidence score, further supporting accurate, explainable diagnostic decision-making.

System Architecture

The AI-enhanced Raman spectroscopy tear analysis system 202 may comprise a compact handheld Raman spectroscopy probe 826, capable of capturing high-resolution spectra from intraocular biomolecules by directing near-infrared excitation light tto the tear film. For clinical stability, especially in settings requiring high reproducibility, the Raman spectroscopy probe 826 may be mounted on a standard ophthalmic slit lamp 204 adapter, which stabilizes both the Raman spectroscopy probe 826 and the patient's eye 802 during examination. The Raman spectroscopy probe 826 optics may include a laser 804 with a focusing lens assembly and an optical filter 824 for rejecting Rayleigh scattered light while capturing inelastic Raman scatter.

Once the Raman signal is collected by a charge-coupled device 808, it may be transmitted through a fiber optic bundle to a spectrometer 810, which digitizes the signal for AI processing. The spectral range of interest typically spans from 400 $cm^{-1}$ to 1800 $cm^{-1}$, encompassing the biochemical fingerprint region where proteins, lipids, glucose, and nucleic acids exhibit characteristic vibrational modes.

At the software layer, the inventions may deploy a tiered artificial intelligence architecture. The raw spectral data may first pass through a denoising pipeline in the spectral data acquisition module 830, which may consist of a stacked autoencoder trained on reference spectra to distinguish meaningful molecular patterns from noise or background fluorescence. This step helps to isolate weak Raman signals from biomarkers.

Following signal cleanup, the processed spectra are analyzed by a convolutional neural network (CNN classifier 920) trained to identify disease-associated spectral patterns. For example, the presence of elevated peaks near 1450 $cm^{-1}$ and 734 $cm^{-1}$ may be classified as indicative of oxidative stress consistent with glaucomatous progression. These biomarkers are used not in isolation, but as part of an AI-generated feature vector, which captures the biochemical context of the sample.

The outputs from the CNN classifier 920 may then be routed to a decision engine that performs multiple tasks: (1) classification of the spectral profile into categories such as normal, early glaucoma, advanced glaucoma, or inflammatory eye disease using the AI/ML interpretation model 924; (2) estimation of individual biomarker concentrations using regression models (e.g., support vector regression, ridge regression) in the concentration estimation module 904; and (3) integration with prior patient data, such as IOP readings and OCT scans, for temporal analysis and trend detection in the report generator 922.

The artificial intelligence engine 828 can also provide a confidence score for diagnostic output that assists in clinical decision-making. (Table 10: AI Models that Provide Confidence Estimates). In one embodiment, the artificial intelligence system utilized for Raman-based glaucoma detection incorporates a mechanism for generating confidence-weighted diagnostic outputs. This functionality is useful for clinical settings, where physicians must be able to assess not only the categorical diagnosis but also the statistical certainty with which it is rendered.

TABLE 10

| AI Models that Provide Confidence Estimates |
|---|
| 1. Probabilistic Neural Networks (PNN)/Softmax Classifiers<br>How it works: Most deep learning models (e.g., CNNs) end with a softmax layer, which outputs probabilities for each class (e.g., healthy vs. glaucoma).<br>Confidence score: The highest probability is used as the model's confidence in its prediction.<br>Use case: Good for quick classification and scalable to multi-class tasks (e.g., stratifying risk into low/moderate/high). |
| 2. Bayesian Neural Networks (BNN)<br>How it works: These models treat weights as probability distributions rather than fixed values, capturing uncertainty in predictions.<br>Confidence score: They naturally output both a prediction and a confidence interval (e.g., "glaucoma: 82% ± 5%").<br>Use case: Excellent when interpretability and uncertainty are meaningful-ideal for medical diagnostics. |
| 3. Monte Carlo Dropout (MC Dropout)<br>How it works: A technique applied to standard deep learning models like CNNs. At test time, dropout is enabled and the model is run multiple times to generate a distribution of outputs.<br>Confidence score: The variance across predictions reflects uncertainty; the average gives the prediction, and the spread gives confidence.<br>Use case: Simple to implement, widely used in medical imaging. |
| 4. Ensemble Models<br>How it works: Multiple independent models (e.g., several CNNs trained with different initializations) are combined.<br>Confidence score: If all models agree, confidence is high; if they disagree, the system reports uncertainty.<br>Use case: Robust predictions, easy to apply to already trained models. |

The core AI/ML interpretation model 924 is based on a convolutional neural network (CNN), optionally combined with recurrent layers for longitudinal data integration. To estimate diagnostic confidence, the system employs Monte Carlo Dropout (MC Dropout) during inference. This technique enables the neural network to simulate Bayesian behavior by stochastically dropping units in the network at test time, resulting in multiple forward passes over the same input data. The variance among these outputs is used to compute a confidence interval around the final classification.

Alternatively, a Bayesian Neural Network (BNN) may be employed to directly model uncertainty. Unlike conventional deterministic networks, a BNN assigns probability distributions to its weights, enabling it to quantify epistemic uncertainty—uncertainty due to limited training data—and aleatoric uncertainty, which is inherent in the spectral measurements themselves.

The AI-enhanced Raman spectroscopy tear analysis system 202 may output both a classification result (e.g., "dry eye," "no dry eye," or "at risk") and a quantified confidence score (e.g., "91% probability±4%"). This output is integrated into the clinician-facing interface, allowing the ophthalmologist to evaluate both the AI's recommendation and the strength of its underlying certainty. In low-confidence scenarios, the interface may recommend retesting, human override, or additional imaging.

To further enhance reliability, an ensemble of models may also be employed. The final diagnostic decision is derived from the consensus or weighted average of predictions made by multiple independently trained models. This ensemble approach reduces overfitting and increases robustness, especially in borderline cases or heterogeneous spectral profiles.

Workflow and User Interface

The Raman spectroscopy diagnostic workflow described herein is optimized for rapid, real-time application during routine clinical assessments. The brief duration and low mechanical force involved in Raman acquisition make this protocol well-tolerated in both screening and diagnostic settings.

For each eye 802, the process begins with Raman spectroscopy probe 826 alignment and patient preparation, which typically takes about ten seconds. One or two drops of a standard ophthalmic anesthetic solution such as proparacaine hydrochloride 0.5% are instilled into the conjunctival sac of the eye to be tested. The anesthetic is allowed to take effect over 60-90 seconds. During this time, the handheld or slit lamp-mounted Raman spectroscopy probe 826 is positioned along the central optical axis of the eye 802, ensuring stable focus on the anterior chamber. Once aligned, Raman excitation is initiated, and spectral data are acquired in approximately five seconds using a low-power laser 804 operating within ANSI-defined ocular safety limits.

TABLE 11

Workflow Timing from Scan Acquisition to Results Display

| Workflow Steps | Estimated Time (seconds) | Cumulative Time (seconds) |
|---|---|---|
| 1. Probe alignment and patient preparation | 10 | 10 |
| 2. Raman excitation and spectral acquisition | 5 | 15 |
| 3. Signal preprocessing (denoising, baseline correction, normalization) | 3 | 18 |
| 4. Spectral analysis and biomarker classification by AI | 2 | 20 |
| 5. Concentration estimation and confidence scoring | 2 | 22 |
| 6. Display of results on user interface | 1 | 23 |

Immediately following acquisition, the raw spectral data may be processed through a real-time signal preprocessing pipeline in the spectral data acquisition module 830. This may include baseline correction, noise filtering, and normalization, all of which are completed within three seconds. The cleaned spectral data may then be analyzed by an AI/ML interpretation model 924 trained to detect and classify disease-relevant biomarkers. This spectral analysis and classification phase takes roughly two seconds. Following classification, a concentration estimation module 904 may calculate the relative abundance of identified biomarkers and generate a confidence score reflecting the integrity and reliability of the scan. These final analytic steps may require an additional two seconds. Finally, the diagnostic output, including biomarker identity, estimated concentration, and interpretive flags, may be rendered by the report generator 922 on the user interface 822 in less than one second.

In total, the full workflow from scan acquisition to result display for a single eye 802 may be completed in approximately 23 seconds, enabling efficient, and chairside diagnostics. For both eyes 802, the procedure can be completed within 40 to 45 seconds, assuming immediate repositioning and consecutive scanning. See Table 11: Workflow Timing from Scan Acquisition to Results Display. In bilateral cases, while scanning time effectively doubles, several computational steps such as preprocessing and inferencing may be parallelized or optimized to reduce total session time. This highly streamlined process supports near-instantaneous diagnostic interpretation, making it well-suited for high-throughput clinical settings and longitudinal patient monitoring.

The user interface 822 of the AI-enhanced Raman spectroscopy tear analysis system 202 may display both the spectral readout and the diagnostic interpretation, including a disease probability score, biomarker concentration table, and a graphical history of changes across multiple visits. Clinicians can review individual spectral features and compare them to normative ranges, enabling personalized treatment planning.

Figure 9:
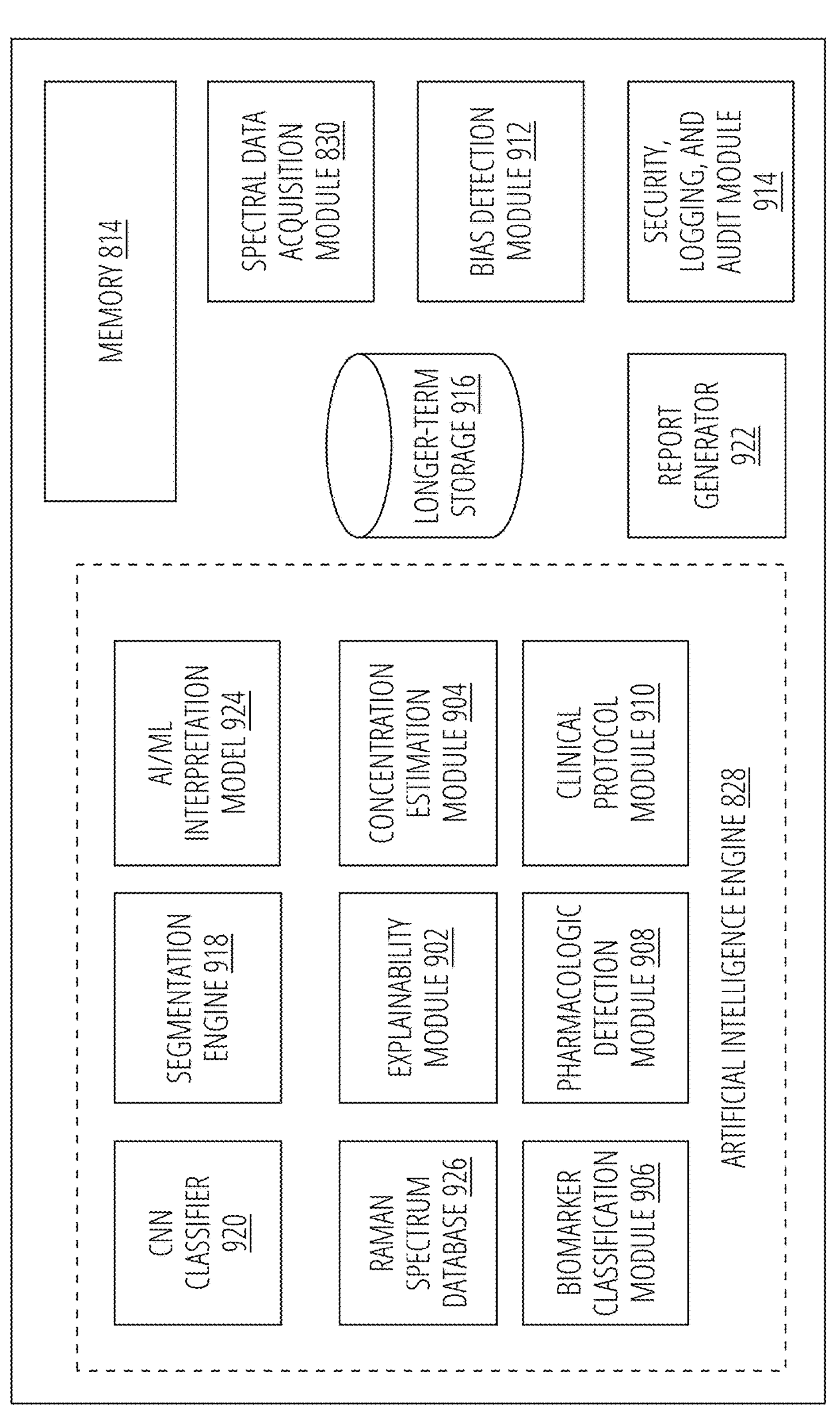
FIG. 9 details the storage aspect of the system architecture of the AI-assisted Raman diagnostic system.

FIG. 9 shows the storage 816 in more detail. What is shown is one or many possible embodiments. Storage 816 may include physical memory 814 and longer-term storage 916 devices. Either the memory 814 or longer-term storage 916 may include non-transitory instructions for the processors 818, either as direct instructions, interpretative instructions, artificial intelligence engines, or artificial intelligence models.

The storage 816 may include a spectral data acquisition module 830 for receiving data from the spectrometer 810 and/or the charge-coupled device 808 and processing this data into a format usable by the artificial intelligence engine 828. The spectral data acquisition module 830 may also collect information on the time the data is received.

The storage 816 could also incorporate a bias detection module 912 to monitor the artificial intelligence engine 828 for data shifts and bias. Should bias be detected, one or more of the models in the artificial intelligence engine 828 may be retrained.

The storage 816 may also include a security, logging, and audit module 914 to maintain compliance with privacy laws and clinical data standards (e.g., GDPR, HIPAA, FDA guidance).

The storage 816 may also include one or more artificial intelligence engines 828 to process the spectral data from the spectral data acquisition module 830 into information useful for clinical diagnosis. The artificial intelligence engine 828 may have a Raman spectrum database 926 (or a plurality of Raman spectrum databases 926) that provides the data from converting the spectral data from the spectral data acquisition module 830 into biomarkers to be used by the AI/ML interpretation model 924.

The artificial intelligence engine 828 may (or may not) have a number of software modules such as one or more CNN classifiers 920, one or more AI/ML interpretation models 924, one or more explainability modules 902, one or more concentration estimation modules 904, one or more biomarker classification modules 906, one or more pharmacologic detection modules 908, and/or one or more clinical protocol modules 910.

The CNN classifier 920 may be based on a convolutional neural network (CNN) or hybrid AI model and is trained on spectra from normal tear film and tear film with diseases. It compares each scan against a reference database to estimate the presence and severity of the anomalies.

The segmentation engine 918 identifies distinct regions of interest (ROI) within the Raman spectrum corresponding to known biochemical classes (e.g., proteins, lipids, small molecules). It applies techniques for spectral detection 108 such as peak detection algorithms, derivative analysis, and adaptive windowing to isolate meaningful intervals for subsequent AI analysis.

The report generator 922 may collect and organize the results of the AI/ML interpretation model 924, the explainability module 902, the concentration estimation module 904, the biomarker classification module 906, the pharmacologic detection module 908, and/or the clinical protocol module 910 into a report for a physician or patient. The report may be sent to the user interface 822.

An Artificial Intelligence/Machine Learning interpretation model 924 ("AI/ML interpretation model 924") may analyze the spectral data to identify molecular patterns associated with diseases. The AI/ML interpretation model 924 may incorporate deep learning algorithms and support adaptive and federated learning models, allowing it to dynamically incorporate newly discovered biomarkers post-deployment.

To support clinical adoption, the artificial intelligence engine 828 may include an explainability module 902, such as Grad-CAM and SHAP, which highlight the precise Raman spectral regions that influenced the model's decision. The explainability module 902 allows clinicians to verify whether a prediction is driven by peak intensity, shape, or molecular degradation pattern.

A concentration estimation module 904 may calculate the relative abundance of identified biomarkers and generate a confidence score reflecting the integrity and reliability of the scan.

The biomarker classification module 906 may be based on a convolutional neural network (CNN) or hybrid AI model and is trained on spectra from normal tear film and tear film with diseases. It compares each scan against a database of biomarkers to estimate the presence and severity of diseases.

The pharmacologic detection module 908 is designed to analyze the presence of drugs within the tear film. This capability enhances diagnostic value by enabling the AI-enhanced Raman spectroscopy tear analysis system 202 not only to detect disease biomarkers, but also to evaluate the ocular pharmacokinetics of therapeutically applied agents.

The clinical protocol module 910 uses the identified biomarkers and the ocular pharmacokinetics to identify treatment options.

Surrogate Biomarkers and Therapeutic Detection

In certain embodiments, the disclosed AI-enhanced Raman spectroscopy tear analysis system 202 is configured not only to detect disease-associated biomarkers, but also to identify and quantify pharmaceutical agents present within the anterior chamber of the eye 802 as surrogate biomarkers. As used herein, a "surrogate biomarker" refers to a pharmacologic substance whose presence, absence, or concentration provides inferential insight into disease activity, therapeutic response, or patient adherence, even if the substance itself is not inherently pathological.

Pharmaceutical agents, whether delivered topically, orally, intravenously, or via intraocular implants, may persist in the tear film in concentrations sufficient to generate identifiable Raman spectral features. These agents include, but are not limited to: Prostaglandin analogs (e.g., latanoprost, bimatoprost), beta-blockers (e.g., timolol), carbonic anhydrase inhibitors (e.g., dorzolamide), alpha-2 adrenergic agonists (e.g., brimonidine), corticosteroids (e.g., prednisolone acetate), immunomodulatory agents, antimetabolites, and investigational biologics.

The AI/ML interpretation model 924 embedded within the AI-enhanced Raman spectroscopy tear analysis system 202 is trained to detect spectral features associated with these compounds and estimate their concentrations using regression models. Upon detection, the AI-enhanced Raman spectroscopy tear analysis system 202 interprets the presence or relative abundance of these compounds as clinical correlates: detection of latanoprost or brimonidine may imply a current or historical diagnosis of glaucoma or ocular hypertension, elevated levels of corticosteroids may indicate active treatment for uveitis, post-surgical inflammation, or immune-mediated conditions, absence of expected pharmacologic signatures, especially when prior treatment is documented, may raise flags for non-adherence or dosing errors.

These pharmaceutical agents act as contextual biomarkers, enabling the AI-enhanced Raman spectroscopy tear analysis system 202 to refine diagnostic interpretations based on therapeutic exposure. The presence or absence of a drug signature can influence how the AI-enhanced Raman spectroscopy tear analysis system 202 classifies disease activity, adjusts confidence metrics, and informs treatment decision support. For example, if a biomarker signature suggests inflammation but corticosteroids are detected within the therapeutic range, the AI output may classify the condition as controlled disease rather than an active flare. The diagnostic output can include the drug name, an estimated concentration, and an assessment of whether the level falls within, above, or below the expected therapeutic range.

The detection method for pharmaceuticals in tear film using Raman spectroscopy can involve spectral acquisition with a 785 nm wavelength laser 804, within a detection range of 400 to 1800 $cm^{-1}$, AI trained to recognize drug-specific Raman peaks, regression models to estimate drug concentration.

This detection capability enables real-time pharmacokinetic assessments, facilitating evaluation of drug absorption, metabolic clearance, and therapeutic efficacy. In this sense, the pharmaceutical agents become dynamic surrogate indicators of clinical state and therapeutic adequacy.

By treating pharmacologic agents as surrogate biomarkers, the AI-enhanced Raman spectroscopy tear analysis system 202 enhances its diagnostic specificity and utility, bridging molecular analysis with real-world treatment context in a non-invasive, real-time platform.

Incorporation of Newly Discovered Biomarkers

To support continued advancement and diagnostic versatility, the disclosed AI-enhanced Raman spectroscopy tear analysis system 202 described herein may be designed to incorporate both existing and newly discovered biomarkers. In clinical research and ophthalmology, biomarker discovery involves analyzing biofluids such as tear film using high-sensitivity spectroscopic or molecular techniques.

When new biomarkers are discovered through clinical studies, biochemical assays, or literature reports, their molecular signatures—including Raman-active vibrational bands—can be characterized and stored in the system's Raman spectrum database 926. The AI/ML interpretation model 924 used within the AI-enhanced Raman spectroscopy tear analysis system 202 may be built with modular training pipelines that allow for supervised fine-tuning on new datasets containing validated spectra from these novel biomarkers. Spectral training data for each biomarker may be augmented through computational techniques such as Gaussian noise injection, synthetic blending, and spectral interpolation to ensure robust pattern recognition.

Upon validation, newly incorporated biomarkers may be included in the biomarker classification module 906 as part of an expanded feature vector, enhancing its ability to diagnose early-stage or atypical disease presentations. A regression sub-model may also be trained to estimate concentration ranges for the newly added biomarker using standard peak intensity mappings and region-specific normalization factors.

These updates may be performed locally on clinical workstations or through federated learning across multiple clinical sites, allowing the AI/ML interpretation model 924 to evolve while preserving patient privacy. In all cases, the AI-enhanced Raman spectroscopy tear analysis system 202 ensures traceability and auditability of model changes through version tracking and validation reporting. As a result, the platform remains capable of adapting to and incorporating subtle, novel biomarkers that reflect emergent understanding of ocular disease.

TABLE 12

| Integration of Newly Discovered Biomarkers |
|---|
| 1. Biomarker Discovery<br>Identification of novel biomarkers through clinical studies, spectroscopic screening, or molecular assays.<br>Candidate biomarkers include cytokines, metabolites, miRNAs, exosomes, and stress-response proteins. |
| 2. Molecular Characterization<br>Spectral analysis to define Raman-active vibrational bands.<br>Verification of diagnostic relevance through correlation with disease states (e.g., glaucoma)<br>Baseline establishment of concentration ranges and expression patterns. |
| 3. Incorporation into System Database<br>Entry of spectral fingerprint into internal reference library.<br>Classification of biomarker by disease association and molecular category.<br>Flag for supervised AI training update. |
| 4. AI Model Retraining and Integration<br>Fine-tuning of neural networks and regression models using new labeled data.<br>Data augmentation applied (noise injection, interpolation, synthetic spectra).<br>Federated learning may be used for privacy-preserving model update across clinics. |
| 5. Diagnostic Deployment and Explainability<br>New biomarker incorporated into real-time classification and quantification workflows.<br>Grad-CAM or SHAP visualizations display spectral regions contributing to predictions.<br>System logs model version and update path for regulatory traceability. |

The inclusion of an explainability module 902, such as Grad-CAM or SHAP, further supports this process by allowing researchers and clinicians to visualize how newly detected spectral features contribute to diagnostic predictions. This transparency ensures that emerging biomarkers can be rapidly evaluated for clinical relevance and integrated into the AI-enhanced Raman spectroscopy tear analysis system 202 without compromising diagnostic consistency or interpretability.

Context-Aware AI Framework

Table 13 Context-Aware Artificial Intelligence: Framework for Raman Spectroscopy shows commonly observed context-aware variables that may require AI adjustment, and Table 14 Systemic Integration Strategies for these Variables provides system integration strategies for these variables. The strategic flow of adjustment, validation, and confidence scoring for the inventions that address the variables is shown in Table 15 AI Flow Description: Context-Awareness Spectral Analysis Pipeline.

TABLE 13

Context-Aware Artificial Intelligence: Framework for Raman Spectroscopy

| Variable | Effect | AI Adjustment Strategy |
|---|---|---|
| Age | Shifts in cytokine, oxidative, and structural biomarker baselines | Include age as input feature; age-stratified models |
| Sex | Hormonal differences impact biomarker expression | Sex-aware thresholds or bias checks |
| Systemic diseases | Affects immune and metabolic markers | Diagnosis flags as input; model calibration |
| Ocular surgery/trauma | Elevated inflammatory markers | Flag cases; modify interpretation window |
| Contact lens wear | May affect tear film diffusion or oxygenation | Exclude or adjust confidence weighting |
| Hydration/ metabolism | Affects metabolic and osmotic balance | Include hydration status if available |
| Post-treatment timing | Alters biomarker pharmacokinetics | Time-aware interpretation |
| Ethnicity/genetics | Baseline differences in TGF-β2, NO levels | Optional demographic feature |
| Ambient light contextual conditions | Affects spectral background | Device self-calibration and AI filtering |
| Device-to-device variance | Hardware inconsistencies | Embed probe-specific calibration metadata |

TABLE 14

| Systemic Integration Strategies for these Variables |
|---|
| Metadata-Aware AI Models: Train models using input matrices that include age, sex, medication, comorbidities, etc.<br>Pre-classification Filter or Flag Layer: A logic layer before final diagnosis that adjusts or annotates predictions based on these factors.<br>Bias Auditing & Fairness Checks: Ensure the model performs equally well across sex, age groups, and ethnic backgrounds. |

TABLE 15

| AI Flow Description: Context-Awareness Spectral Analysis Pipeline |
|---|
| The following flowchart stages define the AI system pipeline: |
| 1. Spectral Input: Raman data is collected from the anterior chamber.<br>2. Contextual Metadata Entry: Patient data such as age, sex, diagnosis, and medication use is entered or retrieved.<br>3. Signal Preprocessing: Raman spectrum is normalized, denoised, and quality-checked.<br>4. Feature Augmentation: Contextual metadata is encoded as input vectors alongside spectral features.<br>5. Model Inference: A context-aware machine learning model evaluates biomarker signatures in the presence of relevant modifiers.<br>6. Confidence Calibration: A reliability score is computed based on signal quality and contextual complexity.<br>7. Output: Diagnostic category, confidence score, and annotation flags are presented to the user. |

Table 16 provides representative embodiments of the AI-enhanced Raman spectroscopy tear analysis system 202, including diagnostic targets, biomarkers, spectral features, and corresponding AI methodologies. Variations lie in analyte targets and AI configurations, while acquisition and analysis workflows remain consistent across embodiments. The embodiments and examples described herein are provided for purposes of illustration and are not intended to limit the scope of the inventions. Variations, modifications, and alternative implementations may be made by those skilled in the art without departing from the spirit and scope of the claimed inventions. The described embodiments demonstrate enablement for representative use cases, but the inventions are not limited to the specific biomarkers, AI models, or spectral features disclosed. Equivalent substitutions and modifications may be made within the scope of the claims.

TABLE 16

AI-Enhanced Raman Spectroscopy Use Cases

| Use Case | Key Biomarkers | Spectral Peaks ($cm^{-1}$) | AI Methodology |
|---|---|---|---|
| Dry Eye Disease | Lactoferrin, Lipocalin, MUC1 | 1450, 1655, 1005 | CNN classification model trained on labeled tear spectra |
| Glucose/ Diabetes | Glucose | 1125, 1340, 1450 | Regression model (e.g., CNN or hybrid DNN) for glucose quantification |
| Drug Monitoring | NSAIDs, Antibiotics | 1235-1600 | Pattern recognition via SVM or CNN trained on pharmaceutical reference spectra |
| Illicit Drug Use | Opioids, THC, Cocaine Metabolites | 750-900, 1350-1550 | Classification using ensemble AI trained on known drug spectra |
| Alcohol Abuse | Ethanol, Acetaldehyde | 880, 1045, 1460 | Threshold-based detection model for ethanol signatures using trained CNN |
| Medical Conditions | Cytokines, Acute-phase proteins | 1200-1600 | Multi-class CNN for systemic condition pattern recognition |
| Glaucoma | MMP-9, TGF-β, Myocilin, NOS, IL-6 | 785, 1450, 1600 | Spectral feature extraction via CNN with glaucoma-specific thresholds |
| Uveitis | IL-6, IL-1β, TNF-α, MCP-1 | 1000-1450 | Inflammation classifier trained on cytokine spectra using CNN/SVM |
| Macular Degeneration | MDA, AGEs, Lutein, CFH | 1000-1600 | Oxidative stress detector using deep learning feature mapping (CNN/autoencoder) |
| Intraocular Tumors | Melanin, Lactate, Cytochrome c, DNA/RNA | 785, 1370-1600, 1740 | Tumor classification network trained on melanin, DNA, and lipid spectral data |

Table 16 provides a comparative matrix summarizing representative use cases enabled by the AI-enhanced Raman spectroscopy tear analysis system 202. Each row corresponds to a distinct diagnostic application, spanning ocular, systemic, metabolic, and pharmacologic domains. For each use case, the matrix identifies the key biomarkers of interest, the Raman spectral peaks associated with those biomarkers, and the specific Artificial Intelligence (AI) methodology employed to interpret the spectral data. For dry eye disease, the AI-enhanced Raman spectroscopy tear analysis system 202 targets tear-based proteins such as lactoferrin, lipocalin, and MUC1. These are detected within characteristic peaks at 1450, 1655, and 1005 $cm^{-1}$, and are analyzed using a convolutional neural network (CNN) trained on spectra from affected and control individuals. In glucose and diabetes monitoring, spectral features associated with glucose are analyzed using a regression model, such as a CNN or hybrid deep neural network, targeting peaks near 1125, 1340, and 1450 $cm^{-1}$. For pharmaceutical drug monitoring, including NSAIDs and antibiotics, a support vector machine (SVM) or CNN is trained on pharmaceutical reference spectra to identify peaks between 1235 and 1600 $cm^{-1}$. Illicit drug detection utilizes an ensemble AI model trained on known spectra of opioids, THC, and cocaine metabolites, focusing on spectral bands in the 750-900 and 1350-1550 $cm^{-1}$ ranges. Alcohol abuse detection involves a CNN-based model trained to recognize ethanol and acetaldehyde at 880, 1045, and 1460 $cm^{-1}$. Medical condition assessment, such as detecting cytokines or acute-phase proteins, uses a multi-class CNN applied to peaks in the 1200-1600 $cm^{-1}$ range.

Glaucoma detection employs spectral feature extraction via CNN with disease-specific thresholds for biomarkers including MMP-9, TGF-β, myocilin, NOS, and IL-6, typically observed at 785, 1450, and 1600 $cm^{-1}$. Uveitis is evaluated through a CNN or SVM trained on inflammatory cytokine profiles such as IL-6, IL-1β, TNF-α, and MCP-1, detected across 1000-1450 $cm^{-1}$. For macular degeneration, oxidative stress markers like malondialdehyde (MDA), advanced glycation end-products (AGEs), and complement factor H (CFH) are identified within the 1000-1600 $cm^{-1}$ range using a CNN or autoencoder model. Lastly, intraocular tumors are assessed through detection of melanin, lactate, cytochrome c, and DNA/RNA signatures, with spectral features at 785, 1370-1600, and 1740 $cm^{-1}$, interpreted by a tumor classification network. This table demonstrates how the AI-enhanced Raman spectroscopy tear analysis system 202 supports broad clinical and biochemical applications, leveraging Raman signal specificity and advanced AI interpretability for precision, sensitivity, and diagnostic utility.

Overview of AI-Enhanced Raman Methodology Overview with Case-Specific Implementations The following generalized AI-Enhanced Raman spectroscopy methodology applies to all described embodiments unless otherwise specified. This framework provides the foundation for sample acquisition, spectral processing, AI-based interpretation, and diagnostic or analytic output. Detailed parameters unique to each example, such as spectral ranges, sample types, AI models, feature extraction methods, and diagnostic thresholds, are further described in the subsections that follow, tailored to specific clinical or analytic contexts.

Dry Eye Disease

In this embodiment, tear fluid is collected and analyzed to detect biochemical imbalances associated with dry eye syndrome. The Raman system targets lipid and protein markers, and a convolutional neural network (CNN) is trained to classify spectra into normal or disease states. Spectral features such as the 1450/1655 $cm^{-1}$ ratio and peaks for mucins and lipocalin are weighted in the classification algorithm.

Glucose/Diabetes Monitoring

This embodiment involves the quantitative measurement of glucose levels in aqueous humor or tear fluid. Spectral features related to glucose ring vibrations are isolated and correlated with reference glucose concentrations. Regression models or hybrid neural networks are used to produce continuous glucose values rather than binary classification.

Drugs/Pharmaceutical Monitoring

Raman spectra from tears are analyzed for the presence of administered pharmaceutical agents, such as anti-inflammatories or antibiotics. Signature spectral peaks for specific drug compounds are detected, and AI is trained on known spectra of drugs in biologic matrices. This enables real-time monitoring of patient compliance or therapeutic pharmacokinetics.

Illicit Drug Use Detection

Spectral analysis is employed to detect the presence of illicit substances or their metabolites in tear film. AI models are trained on labeled spectra from samples containing controlled substances such as opioids, cannabinoids, or stimulants. The detection system can identify trace molecular signatures, supporting point-of-care or forensic applications.

Alcohol Abuse Detection

This use case targets ethanol and related metabolites in tears. Specific vibrational bands corresponding to alcohol presence are monitored. The AI system distinguishes between baseline physiological levels and elevated concentrations indicative of recent alcohol intake.

General Medical Condition Assessment

This broader use case includes AI-Enhanced Raman analysis to identify biomolecular patterns associated with systemic diseases such as infection, autoimmune conditions, or metabolic syndromes. The model may be trained on diverse spectral datasets to classify or flag spectra showing abnormal molecular fingerprints, supporting early screening or diagnostic augmentation.

Glaucoma Biomarker Detection

In this embodiment, Raman spectroscopy is used to analyze aqueous humor or tear fluid to detect biomarkers associated with the development or progression of glaucoma. The AI system is trained to identify and interpret spectral features corresponding to pressure-sensitive molecular changes, oxidative stress markers, and neurodegeneration indicators. Relevant biomarkers include: —Matrix metalloproteinases (e.g., MMP-9)—Transforming growth factor-beta (TGF-β)—Nitric oxide synthase (NOS)—Reactive oxygen species (ROS) byproducts—Myocilin—Interleukins (e.g., IL-6, IL-8)—Neuropeptides (e.g., substance P)

Spectral peaks corresponding to these biomarkers, often in the 1200-1700 $cm^{-1}$ region, are identified through AI-driven feature extraction and correlated with clinical indicators such as intraocular pressure and optic nerve changes. This use case enables early, non-invasive risk assessment and monitoring of glaucoma.

Uveitis Biomarker Detection

In this embodiment, Raman spectroscopy is employed to identify inflammatory biomarkers within the aqueous humor or tear film that are characteristic of uveitis.

AI models are trained to distinguish between inflammatory and non-inflammatory spectra using spectral patterns associated with immune activation and cytokine expression. Key biomarkers include: —Interleukin-6 (IL-6)—Interleukin-1β (IL-1β)—Tumor necrosis factor-alpha (TNF-α)—

Monocyte chemoattractant protein-1 (MCP-1)—Interferon-gamma (IFN-γ)—Prostaglandins (e.g., PGE2). These markers produce characteristic Raman signals in the mid-infrared fingerprint region. AI-based classification enables detection and monitoring of subclinical inflammation, aiding both diagnosis and treatment response evaluation in patients with suspected or confirmed uveitis.

Macular Degeneration Biomarker Detection in Tear Film

This use case involves Raman spectroscopy-based detection of oxidative and metabolic biomarkers in the tear film or ocular fluids related to age-related macular degeneration (AMD). AI algorithms are used to analyze subtle spectral changes associated with retinal oxidative damage and drusen formation. Relevant biomarkers include: —Malondialdehyde (MDA)—Advanced glycation end-products (AGEs)—Carotenoids (e.g., lutein, zeaxanthin)—Complement factor H—Lipofuscin components—Retinal pigment epithelium-derived biomarkers Spectral bands in the 1000-1600 $cm^{-1}$ range are targeted by AI models to identify and quantify early biochemical changes in patients at risk of AMD progression. This enables pre-symptomatic detection and risk stratification.

Macular Degeneration Biomarker Detection Using AI-Enhanced Raman Spectroscopy

The AI-enhanced Raman spectroscopy tear analysis system 202 offers a novel, non-invasive approach for the detection and monitoring of biomarkers associated with age-related macular degeneration (AMD). This application leverages the ability of Raman spectroscopy to detect subtle biochemical changes in the tear film and ocular fluids, which reflect early pathological processes occurring in the retina and retinal pigment epithelium.

Biomarkers associated with AMD include oxidative degradation products such as malondialdehyde (MDA), advanced glycation end-products (AGEs), and lipofuscin-related compounds. These molecules produce distinct vibrational signatures within the 1000-1600 $cm^{-1}$ spectral range, including bands that correspond to carbonyl, amide, and ring structure vibrations. Carotenoids such as lutein and zeaxanthin, essential for retinal health, can also be detected by their characteristic Raman peaks. In addition, complement-related proteins such as complement factor H (CFH), which are implicated in drusen formation and chronic inflammation in AMD, have been correlated with detectable changes in tear biochemistry. Although several AMD-associated biomarkers, such as MDA, AGEs, and carotenoid derivatives, are established in the context of retinal and systemic oxidative stress, their presence in the tear film has only recently garnered investigative attention. The AI-enhanced Raman spectroscopy tear analysis system 202 addresses the core technical challenge of low biomarker concentration in tear fluid by combining Raman signal acquisition with advanced artificial intelligence. AI models, including convolutional neural networks and autoencoders, are trained to recognize weak and potentially obscured biochemical signals by learning discriminative spectral patterns even in noisy or low-signal environments. This allows the AI-enhanced Raman spectroscopy tear analysis system 202 to identify oxidative, inflammatory, or metabolic signatures associated with early AMD, particularly in high-risk individuals, without the need for invasive sampling or costly imaging procedures.

The AI-enhanced Raman spectroscopy tear analysis system 202 integrates Raman spectral acquisition with an artificial intelligence engine that interprets the spectral data using deep learning architectures. These models are trained on a curated dataset of spectra collected from individuals at various stages of AMD as well as from age-matched controls. The AI algorithm learns to distinguish subtle spectral patterns associated with oxidative stress, lipid oxidation, and protein crosslinking. By identifying combinations of peak intensities, ratios, and shifts, such as the carbonyl stretch of MDA near 1720 $cm^{-1}$ and the vibrational bands of carotenoids around 1155-1520 $cm^{-1}$, the AI-enhanced Raman spectroscopy tear analysis system 202 generates a diagnostic output that reflects the biochemical environment correlated with early or progressive AMD.

Clinically, this integrated AI-enhanced Raman spectroscopy tear analysis system 202 enables a new mode of ocular health assessment that can detect the molecular signatures of AMD before structural changes become apparent on imaging modalities such as OCT. This facilitates early intervention, patient risk stratification, and longitudinal monitoring of treatment efficacy. Because the procedure is non-invasive and can be performed rapidly with minimal discomfort, it is particularly well-suited for routine screening and monitoring in elderly populations. The use of feature extraction and ratio-based classifiers enables detection even when the signal intensity is low due to dilution, basal tear turnover, or sampling variability. While early data and modeling affirm the technical feasibility of Raman-based tear analysis for AMD-related biomolecules, this domain represents a fertile and underexplored frontier in ocular diagnostics, one for which the disclosed system is uniquely suited, offering the precision, sensitivity, and analytical intelligence necessary to advance both discovery and clinical validation. The AI-enhanced Raman spectroscopy tear analysis system 202 contributes to this evolving field by providing the necessary analytical precision, spectral sensitivity, and interpretive AI architecture to accelerate the discovery and clinical translation. As such, the system 202 should be understood not only as a diagnostic device but also as a foundational investigative platform for expanding the frontier of tear-based molecular ophthalmology.

Table 17 summarizes representative biomarkers associated with age-related macular degeneration (AMD) that are detectable, or potentially detectable, in the tear film. Each biomarker is paired with literature-based or inferred Raman-active spectral peaks and the associated role of artificial intelligence in enhancing signal interpretation. AI models compensate for weak or noisy signals by applying feature extraction, classification, and dimensionality reduction algorithms tailored to low-concentration analytes in tear film.

TABLE 17

Representative AMD biomarkers detectable in tear film and associated AI analysis

| Biomarker | Tear Presence Evidence | Spectral Peaks ($cm^{-1}$) | AI Analysis Role |
|---|---|---|---|
| Malondialdehyde (MDA) | Detected in tears via spectrophotometric/ oxidative assays | 1720, 1450 | Identifies oxidative stress via peak ratio and pattern learning |
| Advanced Glycation End-products (AGEs) | Suggestive detection in aging or stressed ocular surfaces | 1600, 1370 | Detects carbonyl/ protein-linked glycation patterns |
| Lutein/ Zeaxanthin (metabolites) | Metabolite presence associated with retinal carotenoid levels | 1520, 1155 | Maps antioxidant profiles using CNN-based spectral correlation |
| Complement Factor H (CFH, indirect) | Indirect markers inferred from tear immune profiles | 1445-1500 | Indirectly classifies inflammatory risk states |

TABLE 17-continued

Representative AMD biomarkers detectable in tear film and associated AI analysis

| Biomarker | Tear Presence Evidence | Spectral Peaks ($cm^{-1}$) | AI Analysis Role |
|---|---|---|---|
| Lipofuscin-Derived Components | Under investigation; potential presence in oxidative tear film states | 1340-1420 | Applies autoencoding for weak pattern enhancement and classification |

AI-Enhanced Raman Spectroscopy for Tumor Biomarker Detection in Human Tears

This embodiment describes the use of AI-Enhanced Raman spectroscopy to detect and characterize intraocular tumors, such as uveal melanoma, retinoblastoma, conjunctival carcinoma, and metastatic lesions, through the analysis of tear film biochemistry. The integrated AI-enhanced Raman spectroscopy tear analysis system 202 leverages the spectral sensitivity of Raman scattering to identify molecular signatures associated with malignant transformation and tumor metabolism, while Artificial Intelligence (AI) algorithms enable classification, subtype differentiation, and malignancy risk scoring.

Tears serve as a physiologically rich and non-invasively accessible medium that reflects both local ocular and systemic pathological states. In individuals with intraocular or periorbital malignancies, the tear film can exhibit quantifiable biochemical alterations. These changes include elevation of metabolic byproducts, oxidative stress markers, and tumor-associated proteins that can be detected as distinct Raman spectral shifts.

Key biomarkers detectable in tumor-affected tear samples include:

- Melanin-associated peaks (1370-1600 $cm^{-1}$), relevant in pigmented tumors such as uveal melanoma;
- Nucleic acid vibrations (~785 $cm^{-1}$, ~1330 $cm^{-1}$), reflecting increased cell turnover and DNA/RNA presence;
- Cytochrome c and mitochondrial-associated oxidative stress signatures, indicative of apoptotic dysregulation;
- Lactate (845-875 $cm^{-1}$), consistent with anaerobic metabolism and the Warburg effect;
- Altered lipid-to-protein ratios (~1450 and ~1655 $cm^{-1}$), a marker of membrane remodeling and neoplastic proliferation;
- Tyrosinase and other melanoma-specific enzymes;
- Inflammatory mediators such as MMP-9 and IL-8, often elevated in tumor-associated microenvironments.

The AI-enhanced Raman spectroscopy tear analysis system 202 directs a near-infrared excitation laser 804 (typically 785 nm) at either an in vivo tear meniscus or a microvolume sample obtained non-invasively. The resulting Raman spectrum is preprocessed for background subtraction, noise reduction, and normalization. The cleaned spectral data is then analyzed by a convolutional neural network (CNN), trained on datasets labeled with known tumor and control spectra. The AI model extracts high-dimensional spectral features and maps them to diagnostic probabilities using a softmax-based classification framework.

The AI algorithm is not limited to binary detection. It is designed to differentiate among tumor subtypes and grades, based on composite spectral fingerprints. For example, melanin-rich lesions such as uveal melanoma exhibit distinct peaks that differ from the profiles of lymphoid, squamous, or metastatic tumors. Additionally, features such as mitochondrial dysfunction (cytochrome c shifts), nucleic acid fragmentation, and protein conformational changes contribute to malignancy risk scoring.

In experimental applications, spectra derived from tumor-bearing patients consistently showed alterations in peaks near 1005 $cm^{-1}$ (phenylalanine), 1330 $cm^{-1}$ (nucleic acids), and 1580 $cm^{-1}$ (melanin and tryptophan). These findings are consistent with known metabolic reprogramming in cancerous tissues and underscore the diagnostic relevance of Raman spectral analysis in oncologic ophthalmology.

Beyond detection, the AI-enhanced Raman spectroscopy tear analysis system 202 supports tumor monitoring, identifying progressive molecular changes over time and potentially flagging recurrence. Elevated inflammatory markers, for example, may suggest tumor growth or residual activity. These capabilities position the technology not only as a screening tool, but also as a non-invasive adjunct to imaging and biopsy in longitudinal care pathways.

This tear-based, AI-enhanced Raman platform thus offers a novel diagnostic modality that is both minimally invasive and highly informative, bridging the gap between traditional ophthalmic imaging and molecular oncology. Its integration may reduce dependency on more invasive procedures while supporting earlier intervention, risk stratification, and personalized therapeutic planning for patients with known or suspected intraocular tumors.

Role of AI-Enhanced Raman Spectroscopy in Diagnosing and Monitoring Dry Eye Disease (DED)

Dry Eye Disease (DED) is a multifactorial ocular surface disorder characterized by instability of the tear film, hyperosmolarity, inflammation, and neurosensory abnormalities. It is typically classified into aqueous-deficient, evaporative, or mixed subtypes. Traditional diagnostic approaches, such as Schirmer's test, tear break-up time (TBUT), and fluorescein staining, provide limited insight into the underlying biochemical contributors to disease and often suffer from variability and subjectivity.

This embodiment describes the use of AI-enhanced Raman spectroscopy to diagnose, subtype, and monitor DED by analyzing tear film biochemical composition in a non-invasive manner. Raman spectroscopy enables identification of key molecular components of the tear film, including:

- Lipids (e.g., wax esters and cholesterol esters: ~2850-2900 $cm^{-1}$)
- Proteins (e.g., lactoferrin: ~620-650 $cm^{-1}$; lysozyme: ~990-1005 $cm^{-1}$)
- Mucins (e.g., MUC5AC: ~1200-1250 $cm^{-1}$)
- Inflammatory cytokines (e.g., IL-1β, TNF-α: ~1600-1650 $cm^{-1}$)
- Enzymes and stress markers (e.g., MMP-9: ~1650 $cm^{-1}$; malondialdehyde: ~1720 $cm^{-1}$)
- Electrolyte and osmolarity-related shifts (e.g., $Na^{+}$, $Cl^{-1}$ : 200-400 $cm^{-1}$)

Using a non-contact slit-lamp-mounted or handheld Raman spectroscopy probe 826, the AI-enhanced Raman spectroscopy tear analysis system 202 acquires Raman spectra from the tear film. See FIG. 2 with the Raman module 206 mounted to the slit lamp 204, accompanying an AI processing unit 208. AI-driven spectral analysis enables subtype classification based on biochemical profiles. For example, decreased lipid peaks suggest evaporative DED, while diminished protein content (e.g., lactoferrin and lysozyme) supports aqueous-deficient diagnosis. Inflammatory DED is marked by elevated cytokine- and protease-related spectral features.

Once the subtype is determined, clinicians may tailor treatment accordingly, prescribing lipid-replenishing drops, anti-inflammatory agents, or punctual occlusion. The same AI-enhanced Raman spectroscopy tear analysis system 202 is used for longitudinal monitoring, tracking shifts in tear composition in response to therapy. Early biochemical improvement (e.g., lipid restoration or cytokine reduction) may be detected before subjective symptom relief is reported.

AI models within the AI-enhanced Raman spectroscopy tear analysis system 202 also support flare prediction and personalized trend analysis by comparing serial measurements to baseline values. This enables more proactive and targeted management over time.

The AI-enhanced Raman spectroscopy tear analysis system 202 is particularly useful for high-risk populations such as post-menopausal women, contact lens wearers, autoimmune patients, and individuals undergoing chemotherapy. Its rapid acquisition time, objectivity, and minimal invasiveness make it well-suited for population screening, chairside diagnosis, and follow-up care in both clinical and telehealth settings.

Table 18 presents comparative features, biomarker mapping, clinical use cases, and monitoring outcomes associated with this AI-enhanced Raman spectroscopy tear analysis system 202.

TABLE 18

Biomarker Profiles Detectable in Tear Film by Raman Spectroscopy

| Biomarker | Biochemical Class | Representative Raman Shift ($cm^{-1}$) | Associated DED Subtype(s) | Interpretive Significance |
|---|---|---|---|---|
| Wax Esters/ Cholesterol Esters | Lipid | 2850-2900 | Evaporative | Reflects meibomian gland lipid composition and tear film stability |
| MUC5AC | Mucin (glycoprotein) | 1200-1250 | Mixed/Mucin-deficient | Supports integrity of the mucous layer; reduced in goblet cell dysfunction |
| Lactoferrin | Protein | 620-650 | Aqueous-Deficient | Indicator of lacrimal gland function; often reduced in hyposecretory states |
| Lysozyme | Protein | 990-1005 | Aqueous-Deficient | Reflects antimicrobial tear defense; decreased in lacrimal deficiency |
| Albumin | Protein (plasma-derived) | 1550-1580 | Aqueous-Deficient/ Inflammatory | May indicate epithelial leakage or barrier disruption |
| IL-1β/TNF-α | Cytokine | 1600-1650 | Inflammatory | Markers of immune activation and inflammation |
| MMP-9 | Enzyme (protease) | 1650 | Inflammatory | Associated with epithelial matrix breakdown and inflammation |
| Malondialdehyde (MDA) | Oxidative stress marker | 1720 | Inflammatory/ Mixed | Byproduct of lipid peroxidation; indicates oxidative damage |

Interpretive Summary: Spectral Biomarker Mapping for Subtype Classification in Dry Eye Disease The ability to accurately classify subtypes of Dry Eye Disease (DED) is meaningful for guiding effective and individualized treatment. While traditional diagnostic methods typically assess tear volume or surface damage, they provide limited biochemical insight into the etiology of the disease. Raman spectroscopy, by contrast, enables molecular-level characterization of tear film composition by detecting specific vibrational signatures corresponding to a wide range of biomolecules. Table 18 outlines key tear biomarkers, their Raman spectral ranges, and the DED subtypes they help characterize.

Lipid-associated peaks, particularly in the 2850-2900 $cm^{-1}$ region, correspond to wax esters and cholesterol esters secreted by the meibomian glands. Diminished intensity or spectral irregularity in this region is frequently observed in evaporative DED, where lipid layer deficiency impairs tear film stability. Restoration of these peaks following treatment can serve as a biochemical indicator of improved meibomian gland function.

The MUC5AC mucin, typically secreted by conjunctival goblet cells, appears in the 1200-1250 $cm^{-1}$ range and plays a meaningful role in tear film adherence and mucous layer integrity. Reductions in this glycoprotein's spectral signature are commonly associated with mucin-deficient or mixed DED, reflecting goblet cell loss or dysfunction. As mucin production is not directly evaluated by traditional tests, Raman analysis offers a distinct diagnostic advantage in this domain.

Lactoferrin and lysozyme, detected in the 620-650 $cm^{-1}$ and 990-1005 $cm^{-1}$ regions, respectively, are tear proteins that reflect lacrimal gland output. Their attenuation is a hallmark of aqueous-deficient DED. The presence of albumin, a plasma-derived protein in the 1550-1580 $cm^{-1}$ range, may indicate epithelial barrier disruption or vascular leakage and is often observed in inflammatory or hyposecretory subtypes.

Inflammatory biomarkers such as IL-1β, TNF-α, and MMP-9 occupy overlapping regions in the 1600-1650 $cm^{-1}$ spectral domain, corresponding to amide I and II protein vibrations. Elevated signals in this region are suggestive of active inflammation, epithelial stress, and extracellular matrix degradation. Similarly, malondialdehyde (MDA), a lipid peroxidation product, appears at approximately 1720 $cm^{-1}$ and serves as an indicator of oxidative stress, commonly elevated in both inflammatory and mixed subtypes.

Electrolytes such as sodium and chloride, reflected as a broad band in the 200-400 $cm^{-1}$ region, contribute to tear osmolarity. Hyperosmolarity is a central pathophysiological feature across DED subtypes, and spectral shifts in this region may assist in its non-invasive assessment. Finally, glucose, appearing at 1080-1120 $cm^{-1}$, may be detected in elevated concentrations in patients with systemic metabolic dysregulation, such as diabetes, and may contribute to ocular surface vulnerability.

Together, these biomarker profiles enable spectral subtype classification, offering a more nuanced understanding of disease etiology than is possible with physical testing alone. By mapping the biochemical landscape of the tear film, Raman spectroscopy allows clinicians to distinguish between DED phenotypes and to align therapeutic interventions with molecular findings. This approach supports more precise treatment selection and provides a framework for longitudinal monitoring of disease activity at a molecular level.

TABLE 19

DED-1: Comparison of DED Diagnostic Modalities

| Diagnostic Method | Invasiveness | Biomolecular Insight | Objectivity | Real-Time Output | Subtype Classification | Monitoring Capability | Limitations |
|---|---|---|---|---|---|---|---|
| Schirmer's Test | Moderate | No | Low | No | No | Weak | Tear reflex artifacts, variability |
| Fluorescein Staining | Moderate | No | Subjective | No | No | Weak | Epithelium only, operator dependent |
| Tear Break-Up Time (TBUT) | Low | No | Subjective | No | No | Limited | Inconsistent measurement |
| Osmolarity Testing | Low | Partial | Moderate | Yes | Partial | Limited | Affected by environment |
| Meibography | Low | No | Moderate | Yes | Partial | Limited | Structural only, not functional |
| Interferometry | Low | No | Moderate | Yes | Partial | Weak | Lipid layer only |
| AI-Enhanced Raman Spectroscopy | Low | Yes | High | Yes | Yes | Strong | None of the above limitations |

Interpretive Summary of Diagnostic Modalities for Dry Eye Disease

The clinical assessment of Dry Eye Disease (DED) traditionally relies on a combination of physical and functional tests, many of which provide limited information about the underlying biochemical processes. Table 19 offers a structured comparison of standard diagnostic approaches, outlining their respective characteristics and limitations, as well as the distinct parameters assessed by AI-enhanced Raman spectroscopy.

Common techniques such as Schirmer's test, fluorescein staining, and tear break-up time (TBUT) are valued for their accessibility and familiarity in clinical practice. However, these methods often involve subjective interpretation and may be influenced by variables such as examiner technique, patient response, and environmental conditions. For instance, Schirmer's testing may provoke reflex tearing, while TBUT and staining outcomes can vary based on blink patterns or instillation technique. These tools do not directly capture molecular data and are therefore limited in their ability to classify disease subtypes or detect subtle biochemical shifts.

More recent diagnostic technologies such as osmolarity testing and meibography provide incremental enhancements. Osmolarity devices enable real-time assessment of tear solute concentration, though measurements can fluctuate with environmental exposure and are not specific to the underlying cause of tear film instability. Meibography allows structural imaging of meibomian glands, which can support classification of evaporative DED but lacks the capacity to assess active glandular function or concurrent inflammatory activity.

AI-enhanced Raman spectroscopy introduces a different analytical approach by capturing molecular-level information from tear fluid. It uses vibrational spectroscopy to detect specific biochemical signatures, including proteins, lipids, cytokines, and mucins. When combined with AI-based interpretation, this method can support objective classification of DED subtypes and may be used to monitor biomarker changes over time. In contrast to conventional methods, which rely on physical or structural measurements, this AI-enhanced Raman spectroscopy tear analysis system 202 provides data on the biochemical composition of the tear film from small, non-invasive samples.

Each diagnostic modality plays a role depending on the clinical context. While established tools remain meaningful for structural assessment and routine screening, molecular diagnostic methods such as Raman spectroscopy may offer complementary insights, particularly when evaluating disease heterogeneity, monitoring therapeutic response, or assessing early-stage or subclinical cases. The table underscores the relative differences in invasiveness, objectivity, sensitivity, and specificity across available methods, and illustrates how biochemical techniques may be integrated into broader diagnostic workflows.

TABLE 20

Raman Signature Correlation with DED Subtypes

| DED Subtype | Key Biomarkers (Raman Signature Range) | Representative Spectral Features | Interpretive Implication | Potential Treatment Considerations |
|---|---|---|---|---|
| Evaporative | Lipid degradation products (1430-1470 $cm^{-1}$), reduced wax esters (2850-2900 $cm^{-1}$) | Attenuated lipid band intensity; altered CH-stretching profiles | Indicative of meibomian gland dysfunction and surface instability | Lid hygiene, warm compresses, lipid-based artificial tears, meibomian gland expression |
| Aqueous-Deficient | Reduced lactoferrin (620-650 $cm^{-1}$), lysozyme (990-1005 $cm^{-1}$), elevated albumin 1550-1580 $cm^{-1}$) | Depressed protein peaks, signs of tear volume insufficiency | Suggests lacrimal gland insufficiency and impaired tear production | Tear stimulants (e.g., secretagogues), punctal plugs, preservative-free lubricants |
| Inflammatory | Elevated MMP-9 (~1650 $cm^{-1}$), IL-1β (1600-1650 cm-1), TNF-α (1610-1640 $cm^{-1}$), oxidative stress markers (e.g., MDA at 1720 $cm^{-1}$) | Enhanced amide I/II bands; biomolecular markers of stress | cellulardisruption Indicates active inflammation and epithelial | Topical corticosteroids, cyclosporine A, lifitegrast, antioxidant support |
| Mixed Subtype | Combination of features from above categories | Overlapping lipid/protein alterations and cytokine signatures | Reflects multifactorial etiology requiring comprehensive evaluation | Individualized, multi-targeted therapy addressing each contributing mechanism |

Interpretive Summary: Raman Spectral Correlates of Dry Eye Disease Subtypes

The classification of Dry Eye Disease (DED) into discrete subtypes, evaporative, aqueous-deficient, inflammatory, or mixed, has become meaningful for guiding targeted treatment strategies. However, conventional diagnostic tools are limited in their ability to capture the biochemical underpinnings that distinguish these phenotypes. Table 20 outlines how molecular spectral data derived from Raman analysis may support subtype differentiation based on distinct biomarker profiles.

In the evaporative subtype, Raman spectroscopy frequently reveals attenuation in lipid-associated spectral bands, particularly in the 1430-1470 $cm^{-1}$ region. This corresponds to reduced levels of functional lipids such as cholesterol esters and wax esters secreted by the meibomian glands. Additional changes in the CH-stretching region (2850-2900 $cm^{-1}$) may reflect lipid degradation or altered composition of the tear film lipid layer. These spectral features are consistent with meibomian gland dysfunction, a hallmark of evaporative dry eye. Identification of this profile can inform interventions focused on gland expression and lipid layer restoration.

In aqueous-deficient DED, Raman spectral signatures commonly show reduced intensity in protein bands associated with lactoferrin (620-650 $cm^{-1}$) and lysozyme (990-1005 $cm^{-1}$), proteins typically secreted by the lacrimal gland. Elevated albumin signals around 1550-1580 $cm^{-1}$, possibly originating from increased epithelial permeability or interstitial leakage, may also be present. This spectral constellation supports a diagnosis of lacrimal hyposecretion and tear volume insufficiency. Management strategies in such cases may include tear stimulants, punctal occlusion, or other methods aimed at enhancing tear retention and basal secretion.

Inflammatory DED is characterized by elevated Raman signals in the amide I and II regions (1600-1650 $cm^{-1}$), where pro-inflammatory cytokines such as MMP-9, IL-1β, and TNF-α exhibit diagnostic vibrational signatures. In some cases, oxidative stress markers such as malondialdehyde (MDA) around 1720 $cm^{-1}$ may also be detectable. These spectral features suggest epithelial inflammation, matrix degradation, and oxidative imbalance, frequent drivers of ocular surface damage in inflammatory DED. Early identification of this profile enables initiation of anti-inflammatory or immunomodulatory therapies that might not be indicated for other subtypes.

The mixed subtype presents overlapping spectral features drawn from the three core phenotypes. In these cases, Raman analysis may detect combined lipid degradation, tear protein reduction, and inflammatory marker elevation. The presence of such composite spectral patterns reflects the multifactorial nature of disease in some patients and may necessitate a multimodal treatment approach addressing each contributing mechanism.

Overall, the Raman spectral profiles provide a molecularly resolved framework for DED classification. Unlike conventional tests that rely on structural or volume-based parameters, Raman spectroscopy offers access to the biochemical composition of the tear film. This enables more precise phenotyping, which may in turn facilitate personalized treatment planning and more reliable monitoring of therapeutic outcomes.

TABLE 21

| Monitoring Therapeutic Response with Raman Spectroscopy | | | | | |
|---|---|---|---|---|---|
| Biomarker | Associated DED Subtype | Baseline Spectral Observation | Post-Treatment Spectral Shift | Interpretive Change | Clinical Relevance |
| Wax Esters/ Lipid Bands (2850-2900 $cm^{-1}$) | Evaporative | Reduced intensity, irregular lipid profile | Increased intensity, normalization of lipid spectrum | Suggests improved meibomian gland function | May indicate early lipid layer restoration before symptom relief |
| Lactoferrin (620-650 $cm^{-1}$) | Deficient Aqueous- | Suppressed signal intensity | Signal enhancement toward reference range | output Reflects improved lacrimal gland | Can precede patient-reported improvement in tear volume |
| MMP-9 (~1650 $cm^{-1}$) | Inflammatory | Elevated amide I band intensity | Decreased inflammatory peak amplitude | Reduction in epithelial inflammation markers | May predict reduced flare risk before clinical signs resolve |
| TNF-α/IL-1β (1600-1650 $cm^{-1}$) | Inflammatory | Multiple overlapping peaks elevated | Attenuation of composite cytokine signature | Suggests systemic or localized anti-inflammatory response | Supports objective monitoring of pharmacologic therapy |
| Malondialdehyde (MDA) (1720 $cm^{-1}$) | Inflammatory/ Mixed | Prominent oxidative stress marker | intensity post- Decreased peak antioxidant therapy | Indicates reduced oxidative tissue damage | Can be used to validate effect of adjunctive antioxidant use |

Interpretive Summary: Monitoring Therapeutic Response Using Raman Spectroscopy

The dynamic nature of Dry Eye Disease (DED) necessitates diagnostic modalities capable of detecting subtle, often subclinical, biochemical changes over time. Traditional assessments, such as symptom questionnaires, fluorescein staining, and tear break-up time, are useful for initial evaluation but often lag behind molecular events that indicate therapeutic efficacy or disease progression. Table 21 outlines how specific spectral biomarkers observed through Raman analysis may reflect early biochemical responses to therapy across distinct DED subtypes.

For evaporative DED, characterized by meibomian gland dysfunction, spectral features in the CH-stretching region (2850-2900 $cm^{-1}$) can reveal restoration of lipid layer integrity. Baseline spectra frequently show reduced wax ester intensity or irregular lipid profiles, which improve following interventions such as gland expression or lipid-based artificial tear supplementation. These changes may occur before patients report subjective symptom relief, thereby providing an early indicator of therapeutic impact.

In aqueous-deficient DED, Raman signatures associated with lactoferrin (620-650 $cm^{-1}$) and lysozyme reflect lacrimal gland function. Restoration of these protein peaks following treatment (e.g., punctal occlusion or tear stimulants) can signal improved tear volume. This spectral recovery may precede changes in Schirmer's test scores or patient-perceived lubrication, making Raman analysis a potentially more sensitive monitoring modality.

In cases of inflammatory DED, spectral features in the amide I region (~1600-1650 $cm^{-1}$), corresponding to MMP-9, IL-1β, and TNF-α, serve as molecular indicators of inflammatory activity. Effective anti-inflammatory therapy is often associated with attenuation of these peaks. Similarly, reductions in malondialdehyde (MDA) at 1720 $cm^{-1}$, a biomarker of oxidative stress, can indicate improved ocular surface integrity following antioxidant or anti-inflammatory intervention. These molecular shifts provide objective evidence of therapeutic response that may not yet be apparent on slit lamp 204 examination or symptom scoring.

The interpretive change column in Table 21 highlights how Raman-detected spectral shifts correspond to clinical processes such as reduction in cytokine load, restoration of tear lipid composition, or reconstitution of tear film proteins. These changes offer a molecular correlate to therapeutic success and may inform decisions regarding continuation, escalation, or tapering of treatment.

Taken together, Raman spectroscopy allows for biochemical validation of clinical management strategies, bridging the gap between subjective symptom assessment and objective molecular evidence. This temporal sensitivity enhances the precision of DED care by enabling earlier and more individualized assessment of treatment response, particularly in patients with complex or overlapping disease subtypes.

TABLE 22

Monitoring Therapeutic Response with Raman Spectroscopy

| Biomarker | DED Subtype | Baseline Raman Finding | Post-Treatment Raman Finding | Associated Spectral Range ($cm^{-1}$) | Clinical Implication |
|---|---|---|---|---|---|
| Wax Esters/ Cholesterol Esters | Evaporative | Attenuated lipid bands, irregular CH-stretching | Increased lipid band intensity and normalization | 2850-2900 | Suggests improved lipid layer quality before symptom resolution |
| Lactoferrin | Aqueous-Deficient | Reduced signal intensity | Enhanced spectral peak toward physiological levels | 620-650 | Indicates restoration of lacrimal gland protein secretion |
| MMP-9 | Inflammatory | Elevated amide I band (matrix degradation marker) | Reduced amplitude of inflammatory peak | 1650 | Suggests resolution of epithelial inflammation |
| IL-1β/TNF-α | Inflammatory | Prominent cytokine-related peaks in amide range | Decreased peak density and amplitude | 1600-1650 | Reflects downregulation of inflammatory cytokines |
| Malondialdehyde (MDA) | Inflammatory/ Mixed | Increased oxidative stress signature | Diminished peak after antioxidant or anti-inflammatory therapy | 1720 | Supports reduced lipid peroxidation and oxidative tissue stress |
| Albumin | Aqueous-Deficient/ Inflammatory | Detectable leakage-associated peak | Attenuation or normalization post-treatment | 1550-1580 | May indicate improved epithelial barrier integrity |

Clinical Scenario: Integrated Osmolarity, Raman Spectroscopy, and AI Analysis

A 57-year-old female patient presents to a dry eye clinic with complaints of burning, fluctuating vision, and ocular fatigue, which worsen in the evening. She has a history of type 2 diabetes and mild rosacea. A tear osmolarity test shows values of 317 mOsm/L in the right eye and 309 mOsm/L in the left, suggesting hyperosmolar tear film instability.

To further characterize the ocular surface condition, a Raman spectroscopy scan of the tear film is performed using a non-contact Raman spectroscopy probe 826. The Raman spectrum reveals decreased intensity in the lysozyme region (~1003 $cm^{-1}$), elevated peaks near 1445 $cm^{-1}$ associated with lipid changes, and inflammatory markers in the amide I band (~1650 $cm^{-1}$). These spectral signatures align with biochemical changes linked to chronic dry eye in diabetic patients.

AI-based analysis integrates these Raman features with the osmolarity data and the patient's clinical metadata (diabetes duration, meibomian gland dysfunction, OSDI symptom score). The AI-enhanced Raman spectroscopy tear analysis system 202 stratifies the patient as high-risk for progressive evaporative and inflammatory dry eye and recommends escalation from artificial tears to anti-inflammatory therapy.

Over a 6-week follow-up, sequential Raman scans and osmolarity tests show stabilization: osmolarity drops to 304 mOsm/L bilaterally, and Raman signatures normalize in lipid and protein bands. The AI system confirms biochemical improvement, supporting the decision to maintain the current therapy.

This scenario illustrates how the combined use of tear osmolarity, Raman spectroscopy, and AI can guide precise diagnosis, personalize treatment, and validate therapeutic response in complex ocular surface disease.

The methodology applied in this embodiment is supported by the generalized AI-enhanced Raman spectroscopy framework described in the Methodology section. Specific biomarkers and representative spectral peaks relevant to this use case are summarized in Table 22, which provides a unified reference for embodiments disclosed herein.

Interpretive Summary: Spectral Biomarker Shifts as Indicators of Therapeutic Response in DED The management of Dry Eye Disease (DED) may require not only accurate diagnosis but also ongoing evaluation of therapeutic effectiveness. Traditional assessment methods, such as symptom questionnaires, fluorescein staining, or tear film breakup time, often depend on patient reporting or surface-level examination, both of which may lag behind biochemical improvements. Table 22 highlights the capacity of Raman spectral biomarkers to provide earlier, more objective insight into molecular changes associated with treatment response.

In evaporative DED, meibomian gland dysfunction often results in lipid layer insufficiency. This condition is reflected spectrally as attenuation in CH-stretching bands within the 2850-2900 $cm^{-1}$ range. Following interventions such as thermal pulsation or lipid-based tear supplementation, Raman spectroscopy may detect early normalization of lipid signals, even before patients perceive symptomatic improvement. This observation supports the potential of Raman-based lipid monitoring as an early indicator of treatment success.

In cases of aqueous-deficient DED, biomarkers such as lactoferrin, found in the 620-650 $cm^{-1}$ range, serve as surrogates for lacrimal gland output. A suppressed signal at baseline that increases post-treatment suggests reactivation of glandular protein secretion, potentially in response to tear stimulants or punctal occlusion. These spectral changes may precede or occur independently of measurable changes in Schirmer scores or subjective comfort levels.

Inflammatory DED is characterized by elevated pro-inflammatory cytokines and proteases, which present as enhanced amide I and II bands, especially in the 1600-1650 $cm^{-1}$ range. Biomarkers such as MMP-9, IL-1β, and TNF-α frequently contribute to these signals. A post-treatment reduction in peak amplitude indicates downregulation of inflammatory activity, which may reflect pharmacologic efficacy before surface staining or redness improves. Similarly, attenuation of the malondialdehyde (MDA) peak at 1720 $cm^{-1}$, a marker of oxidative stress, suggests reduced lipid peroxidation and cellular damage.

The presence and magnitude of albumin in the 1550-1580 $cm^{-1}$ region provide indirect insight into epithelial barrier integrity. Its reduction following treatment may indicate resolution of subclinical surface permeability, which would otherwise remain undetected in routine clinical evaluations.

Overall, the spectral shifts observed in Raman biomarker signatures represent a biochemical timeline that may precede, and in some cases predict, structural or symptomatic improvement. These molecular changes offer clinicians a real-time, quantifiable measure of therapeutic response, enabling earlier decision-making regarding treatment adjustment or continuation. Furthermore, such data may support the use of Raman spectroscopy as a non-invasive monitoring tool in longitudinal care plans for patients with complex or treatment-resistant DED.

Interpretive Summary: Strategic Screening Applications for AI-Raman Dry Eye Diagnostics Dry Eye Disease (DED) is a heterogeneous and frequently underdiagnosed condition with multifactorial causes and varying clinical presentations. Despite its high prevalence, especially in specific at-risk groups, many cases remain undetected until symptoms become moderate to severe. Table 23 highlights selected populations with elevated susceptibility to DED, outlining both the underlying risk contexts and the potential value of Raman-AI-based screening.

Post-menopausal women represent a well-established risk group due to hormonal shifts, particularly reductions in estrogen and androgen levels that influence lacrimal gland function and meibomian gland lipid secretion. In this population, Raman-AI screening can aid in the early detection of subclinical dry eye by monitoring protein and lipid biomarkers that respond to hormonal modulation. Integration into routine eye exams could facilitate timely intervention before symptoms or irreversible surface damage emerge.

Contact lens users are another group commonly affected by DED, largely due to mechanical disruption of the tear film and changes in blink behavior. Raman analysis offers an objective method to evaluate lipid layer degradation and mild inflammatory activation, key contributors to contact lens intolerance. Screening during lens fitting or follow-up may reduce discontinuation rates and improve long-term lens tolerance.

Patients with autoimmune disorders, including Sjögren's syndrome and rheumatoid arthritis, are at high risk for aqueous-deficient dry eye and chronic ocular inflammation. For these individuals, Raman-AI platforms can support longitudinal monitoring of cytokine and tear protein profiles, providing a biochemical complement to clinical assessment.

TABLE 23

Use Cases and Target Populations for AI-Raman Screening

| Target Population | Risk Factors/ Clinical Context | Potential Diagnostic Benefit | Raman-AI Application | Clinical Integration Opportunity |
|---|---|---|---|---|
| Post-Menopausal Women | Hormonal changes affecting tear composition and gland function | Early detection of subclinical dry eye and lacrimal dysfunction | Biomarker-based profiling for estrogen-related changes in tear film | Routine screening in primary eye care for age-related DED |
| Contact Lens Wearers | Mechanical irritation and altered tear dynamics | Prevention of contact lens intolerance via early detection | Monitoring lipid layer degradation and inflammation markers | Integration into contact lens fitting or follow-up visits |
| Patients with Autoimmune Disease (e.g., Sjogren's, RA) | High risk of aqueous-deficient dry eye and ocular inflammation | Monitoring disease-related tear deficiency and flare-up risk | Tracking tear protein and cytokine profiles longitudinally | Adjunct to rheumatologic management and ocular comorbidity tracking |
| Chemotherapy or Radiation Patients | Toxic effects on lacrimal and meibomian glands | Early intervention to preserve ocular surface integrity | Detection of reduced glandular protein secretion | Supportive care pathway in oncology or survivorship clinics |
| Heavy Digital Device Users | Reduced blink rate and evaporative stress | Assessment of evaporative DED before visual symptoms manifest | Detection of lipid and osmolarity imbalance in tear film | Workplace screening or telemedicine integration |
| Post-Refractive Surgery Patients | Surgical disruption of corneal nerves affecting tear feedback | Monitoring for post-operative DED and nerve regeneration trends | Biochemical follow-up of protein and lipid markers | Postoperative care algorithm for LASIK and PRK patients |

This approach may help identify impending flare-ups or guide adjustments to immunosuppressive therapy.

Patients undergoing chemotherapy or head/neck radiation often experience toxicity-induced glandular damage, which compromises both tear production and composition. Raman biomarkers such as lactoferrin, albumin, and oxidative stress indicators can detect tear film abnormalities before the onset of symptomatic surface disease. The integration of Raman-based monitoring into oncology support programs may help protect ocular surface health during and after treatment.

The rise in digital device usage has introduced a growing cohort of patients with environmentally or behaviorally driven evaporative DED. Prolonged screen time reduces blink frequency, destabilizing the lipid layer. Raman analysis of lipid-related spectral bands and osmolarity-associated features provides a method to identify early tear film disruption before chronic discomfort or vision changes develop. This use case is particularly well-suited to occupational health screening and telemedicine contexts.

Finally, post-refractive surgery patients are vulnerable to DED due to corneal nerve transection, which affects sensory feedback to the lacrimal gland. Raman-AI systems can track recovery trends in tear film biochemistry, including lipid replenishment and normalization of inflammatory markers. This capability allows for more individualized follow-up and may guide adjunctive treatments aimed at supporting neural regeneration and tear film recovery.

In sum, this table demonstrates how Raman-AI screening could complement existing clinical pathwaysby addressing populations for whom traditional diagnostics are either underutilized or insufficiently sensitive. The platform's ability to detect biochemical deviations prior to structural or symptomatic manifestations enhances its utility in both preventive and longitudinal care strategies.

The AI-enhanced Raman spectroscopy tear analysis system 202 may be incorporated into standard clinical or veterinary diagnostic workflows as follows:

1. Patient Presentation—The subject (human or animal) presents with ocular symptoms, systemic risk factors, or as part of routine screening.
2. Baseline Evaluation—Conventional assessments such as the Ocular Surface Disease Index (OSDI), Schirmer's test, tear break-up time (TBUT), and lid margin evaluation may be performed.
3. Tear Sampling—A tear film sample is collected either in vivo via a slit-lamp-mounted probe or ex vivo using a capillary microvolume collection tube.
4. Raman Acquisition—A near-infrared Raman excitation beam (e.g., 785 nm) is directed at the sample. The scattered signal is acquired through a spectral detection module.
5. AI Analysis—The spectrum is preprocessed and analyzed by the artificial intelligence engine 828, which classifies the sample into one or more diagnostic categories and calculates a confidence score.
6. Therapeutic Decision-Making—The clinical user may view spectral interpretations and biomarker insights to guide therapy. This may include anti-inflammatory agents, lipid supplements, or further investigation for suspected neoplasia.
7. Monitoring and Follow-Up—At follow-up visits, repeated Raman analysis enables tracking of treatment response, risk of flare, and disease stability.

Interpretive Summary: Clinical Integration of Raman-AI Diagnostics in the Management of Dry Eye Disease The evaluation and management of Dry Eye Disease (DED) have traditionally relied on a constellation of subjective symptom assessments and surface-level functional tests. While helpful, these approaches often fall short in providing a reliable biochemical profile of the disease, limiting their ability to stratify patients, detect early pathology, or guide treatment decisions with precision. The AI-enhanced Raman spectroscopy tear analysis system 202 presents a structured overview of how Raman spectroscopy, when integrated with artificial intelligence, can augment the clinical pathway, from initial presentation to long-term management.

At the point of patient presentation, the workflow begins in familiar territory: eliciting symptoms, reviewing visual complaints, and identifying risk factors such as extensive screen use, autoimmune conditions, or systemic medication use. This contextual foundation remains meaningful to guide subsequent testing and interpretation.

The baseline assessment stage includes standard diagnostic elements such as the Ocular Surface Disease Index (OSDI), tear breakup time (TBUT), Schirmer's test, fluorescein staining, and examination of the lid margins and meibomian glands. These evaluations provide a functional and anatomical snapshot of tear film integrity and ocular surface status.

It is at the Raman spectroscopy stage that the workflow diverges meaningfully from conventional models. A small, non-invasive tear sample is analyzed to generate a molecular fingerprint of the tear film, including lipids, proteins, mucins, and inflammatory cytokines. These spectral data are processed through AI algorithms capable of identifying disease subtypes, evaporative, aqueous-deficient, inflammatory, or mixed, based on multivariate biomarker patterns rather than isolated measurements. This shift from symptom-based categorization to biochemical subtype classification marks a significant advancement in DED diagnostics.

During treatment decision-making, clinicians can match interventions to the underlying molecular etiology revealed by Raman-AI analysis. For example, a patient with elevated MMP-9 or TNF-α may benefit from anti-inflammatory therapy, while a lipid-deficient profile may warrant gland-targeted approaches or lipid-based lubricants. This targeted alignment of therapy to tear film composition enables more rational and potentially more effective clinical decisions.

The monitoring and follow-up phase leverages the reproducibility of Raman spectroscopy to assess changes in biomarker profiles over time. By re-testing at clinically relevant intervals, providers can determine whether a selected therapy is modulating the biochemical environment in the intended direction. This capability reduces reliance on subjective symptom fluctuation and provides a more stable basis for therapeutic adjustment.

In the context of long-term management, AI-enhanced Raman platforms offer the opportunity to build individualized biomarker baselines and longitudinal trend maps. These data can be used to anticipate inflammatory flares, assess treatment durability, and personalize maintenance regimens. Informed discussions with patients can also be enriched by visual and molecular data, supporting education and adherence.

In sum, the workflow described for the AI-enhanced Raman spectroscopy tear analysis system 202 illustrates how Raman-AI systems can be integrated into everyday clinical practice. Rather than replacing traditional tools, they enhance decision-making through objective, molecular insight. Their application spans the continuum of care, from early detection to real-time treatment monitoring, and may ultimately facilitate a shift toward more precise, personalized, and data-driven management of Dry Eye Disease.

TABLE 24

AI-Enhanced Raman Spectroscopy vs. Traditional Dry Eye Diagnostic Tools

| Feature | Raman Spectroscopy | Traditional Tools (Schirmer, TBUT, Staining) |
|---|---|---|
| Invasiveness | Non-contact or minimally invasive (microdrop tear sample) | Invasive (strip, dye, physical contact) |
| Measurement Type | Molecular composition (lipids, proteins, cytokines) | Physical/functional (tear volume, break-up, staining) |
| Sensitivity | High (picomolar detection possible with SERS) | Low to moderate |
| Specificity | High-can distinguish between DED subtypes | Low-does not reveal cause (e.g., aqueous vs evaporative) |
| Subjectivity | Objective (spectral data + AI classification) | Often subjective (clinician interpretation, lighting) |
| Speed | Rapid (<2 min per sample with modern devices) | Moderate (~5-10 min including wait times) |
| Treatment Monitoring | Tracks biochemical changes with therapy | Indirect changes; limited ability to quantify improvement |
| Early/Subclinical Detection | Yes-detects molecular shifts before symptoms arise | No-usually only positive after structural changes |
| Repeatability/ Reproducibility | High with controlled sampling and AI processing | Variable-depends on operator, tear volume, blink pattern |
| Use in Personalized Medicine | Yes-guides subtype-specific treatment | Limited-often leads to generic therapy |

Interpretive Summary: Comparative Advantages of AI-enhanced Raman Spectroscopy in Dry Eye Disease Evaluation The diagnosis and management of Dry Eye Disease (DED) have historically relied on physical and functional assessments such as Schirmer's testing, tear break-up time (TBUT), and ocular surface staining. While these methods are clinically accessible and familiar, they possess inherent limitations in sensitivity, specificity, and reproducibility. Table 24 presents a comparative analysis that delineates the advantages of Raman spectroscopy, particularly in its surface-enhanced and AI-integrated format, relative to conventional diagnostic approaches.

Invasiveness is a fundamental consideration in patient compliance and diagnostic utility. Traditional methods often require physical contact with the ocular surface via filter paper strips, fluorescein dye, or examination under cobalt blue light. These procedures can cause reflex tearing or discomfort, which may confound test results. Raman spectroscopy, by contrast, uses a non-contact or minimally invasive approach, requiring only a microdroplet of tear fluid for analysis, thereby improving patient comfort and minimizing physiologic interference.

The measurement type further distinguishes the two paradigms. Traditional diagnostics evaluate structural disruption (e.g., staining) or functional outputs (e.g., tear volume, stability), but they provide limited insight into the underlying biochemical causes of disease. Raman spectroscopy captures molecular composition, detecting lipids, proteins, mucins, and cytokines that inform not only the presence of disease but also its subtype and severity.

Sensitivity and specificity are meaningful for early and accurate detection. Raman spectroscopy, particularly in its surface-enhanced Raman scattering (SERS) format, can detect tear components at picomolar concentrations, far exceeding the detection thresholds of conventional tools. Moreover, by recognizing specific spectral signatures, Raman methods can distinguish between evaporative, aqueous-deficient, and inflammatory subtypes of DED. Traditional tests lack this biochemical resolution and generally do not identify the etiology of disease, often leading to non-specific treatment.

The objectivity of AI-enhanced Raman analysis is another distinguishing feature. Traditional tests often rely on visual interpretation under variable lighting and depend heavily on the examiner's experience. In contrast, Raman-generated spectra can be analyzed algorithmically, reducing inter-operator variability and supporting more standardized decision-making.

Speed is also favorable with Raman methods, as modern devices can generate and analyze tear spectra in under two minutes. This compares favorably with the cumulative time required for staining, dye clearance, and subjective evaluation in traditional workflows.

In terms of treatment monitoring, Raman spectroscopy enables clinicians to track biochemical changes over time. For example, reductions in inflammatory biomarkers or restoration of lipid signals can be observed before clinical symptoms resolve. Traditional methods, in contrast, provide only indirect evidence of change and are poorly suited to quantitative therapeutic monitoring.

The ability of Raman tools to detect subclinical disease is particularly valuable in patients with fluctuating or early-stage DED. Subtle molecular shifts may precede observable staining or volume changes, offering a window for early intervention. Conventional tests typically yield positive findings only after anatomical disruption has occurred.

Repeatability and reproducibility of Raman spectroscopy, especially when integrated with AI for spectral normalization, are higher than those of blink-sensitive or environmentally influenced functional tests. Finally, the integration of Raman data into personalized medicine frameworks enables targeted therapeutic decisions based on biomarker profiles, rather than empirical or trial-and-error treatment.

In sum, the comparison presented in Table 24 underscores a transition from structural to molecular diagnostics in ocular surface disease. While traditional tools remain useful for gross assessment, Raman spectroscopy expands the diagnostic landscape by offering reproducible, high-resolution biochemical insight that supports individualized and temporally responsive care.

Clinical Case Scenario: Improving Dry Eye Management with AI-Enhanced Raman Spectroscopy A 62-year-old female presents to the ophthalmology clinic with a six-month history of ocular dryness, intermittent blurred vision, and a burning sensation exacerbated by screen use. She has a history of hypothyroidism and is postmenopausal. Prior treatment with over-the-counter artificial tears has offered minimal relief. Slit lamp 204 examination reveals mild conjunctival injection and debris along the lid margin. Schirmer's test shows borderline values, and tear break-up time is below average. The findings are suggestive but not definitive for Dry Eye Disease, and the subtype remains unclear.

To clarify diagnosis and guide therapy, a tear sample is collected using a disposable microfluidic SERS cartridge, and Raman spectral analysis is immediately performed. Within seconds, the AI-enhanced Raman spectroscopy tear analysis system 202 identifies a molecular signature consistent with evaporative dry eye due to meibomian gland dysfunction. Elevated lipid degradation products and an increased IL-1β signal confirm the presence of ocular surface inflammation. A personalized biomarker report is generated and displayed on the display screen 210.

Based on this output, the clinician initiates targeted therapy: warm compress treatment, omega-3 supplementation, and a short course of topical anti-inflammatory medication. Four weeks later, repeat Raman testing shows a reduction in inflammatory cytokines and improved lipid spectrum homogeneity, even before symptom improvement is subjectively reported by the patient.

This case highlights how AI-enhanced Raman spectroscopy can provide immediate, objective, and molecularly specific data to support the diagnosis and monitoring of Dry Eye Disease. It enables subtype classification, confirms treatment efficacy, and allows for data-driven therapeutic decisions, all through a rapid, non-invasive, and repeatable testing method.

The methodology applied in this embodiment is supported by the generalized AI-enhanced Raman spectroscopy framework described in the Methodology section. Specific biomarkers and representative spectral peaks relevant to this use case are summarized in Table 22, which provides a unified reference for embodiments disclosed herein.

Clinical Use Case: Tear-Based Detection of Diabetes and Systemic Metabolic Dysregulation Tear fluid contains metabolite signatures reflective of both local ocular health and systemic physiological conditions. This embodiment describes the use of AI-enhanced Raman spectroscopy to identify spectral biomarkers in human or animal tear film associated with metabolic dysregulation, with a primary focus on diabetes mellitus.

In individuals with diabetes, hyperglycemia and systemic oxidative stress induce compositional changes in tear film. Raman spectral analysis of tear samples reveals quantifiable differences in the following biochemical features:

- Glucose (~1080-1120 $cm^{-1}$): Elevated Raman signal intensity corresponding to glucose vibrational modes.
- Lactate (~845-875 $cm^{-1}$): Byproduct of anaerobic glycolysis, often elevated in poorly controlled diabetes.
- Albumin (~1550-1580 $cm^{-1}$): May appear in increased concentrations due to altered vascular permeability.
- Malondialdehyde (MDA) (~1720 $cm^{-1}$): Lipid peroxidation marker indicating oxidative tissue stress.
- Altered lipid-to-protein ratio (~1450-1655 $cm^{-1}$): Reflects systemic membrane remodeling and protein glycation.

The AI-enhanced Raman spectroscopy tear analysis system 202 directs a Raman excitation beam at the tear film, either in vivo or using a small ex vivo sample. The resulting spectrum is analyzed by an AI model trained on spectra from both diabetic and non-diabetic subjects. The model classifies spectra based on feature vectors derived from the glucose region, oxidative stress markers, and lipid/protein balance.

By detecting metabolic shifts at the ocular surface, the AI-enhanced Raman spectroscopy tear analysis system 202 provides a minimally invasive tool for diabetes screening, risk stratification, and therapeutic monitoring. Its ability to identify biochemical change without requiring blood draw or fasting makes it especially valuable for pediatric, elderly, or non-compliant populations.

In longitudinal use, the AI model can track fluctuations in tear glucose and lactate levels over time, correlating with systemic glycemic control and enabling early detection of glycemic excursions. The AI-enhanced Raman spectroscopy tear analysis system 202 may also support identification of pre-diabetic metabolic trends or inflammatory comorbidities, including diabetic retinopathy, through shifts in cytokine and oxidative stress biomarkers.

This tear-based, AI-Enhanced approach complements existing glucose monitoring strategies and may serve as an adjunct in endocrinology, primary care, and ocular health contexts. It may also be adapted for veterinary endocrinology in non-human mammals presenting with hyperglycemia or insulin resistance.

TABLE 25

Biomarkers in Tears of Patients with Diabetes

| Biomarker | Relative Quantity in Diabetic Tears | Clinical Relevance/ Observation | Representative Raman Shift ($cm^{-1}$) | Biological Origin |
|---|---|---|---|---|
| Glucose | High | Correlates with blood glucose; marker for glycemic control | 1080-1120 | Systemic circulation |
| Advanced Glycation End Products (AGEs) | High | Indicates oxidative stress and protein glycation | 1350-1375 | Protein modification products |
| Albumin | Medium-High | Leakage due to microvascular damage | 1550-1580 | Plasma leakage |
| Lactoferrin | Low | Reduced tear antimicrobial defense in diabetes | 620-650 | Lacrimal gland |
| Lysozyme | Low | Impaired innate immunity; increased infection risk | 990-1005 | Lacrimal gland |
| MUC5AC | Low | Goblet cell dysfunction; altered mucin layer | 1200-1250 | Conjunctival goblet cells |
| Urea | High | Reflects systemic metabolic imbalance | 1000-1050 | Plasma-derived |
| Cytokines (e.g., IL-6, TNF-α) | High | Increased inflammatory signaling | 650-750 (broad) | Immune cells |
| Sorbitol | High | Byproduct of aldose reductase pathway; linked to damage | 860-880 | Polyol pathway metabolite |
| Lipids | Altered | Tear film instability due to Meibomian dysfunction | 1430-1470 | Meibomian glands |

Clinical Applicability in Patients with Diabetes

The AI-enhanced Raman spectroscopy tear analysis system 202 offers significant diagnostic and monitoring potential for patients with diabetes mellitus. In individuals with diabetes, metabolic dysregulation results in altered tear composition, including elevated glucose, advanced glycation end products (AGEs), and inflammatory markers. These biochemical deviations can be non-invasively detected and quantified through Raman spectral analysis of the tear film.

The AI-enhanced Raman spectroscopy tear analysis system 202 utilizes a contactless or minimally invasive Raman spectroscopy probe 826 to analyze tear samples from the ocular surface. The artificial intelligence engine 828 identifies diabetes-associated spectral features such as:

- Increased glucose content (noted around 1080-1120 $cm^{-1}$)
- Presence of AGEs and protein modifications (1350-1375 $cm^{-1}$)
- Changes in albumin levels due to vascular leakage
- Depletion of antimicrobial proteins like lactoferrin and lysozyme These findings are interpreted in real time using a multi-tiered AI architecture that classifies tear spectra based on known diabetic profiles. The AI model is trained on a reference library of Raman spectra from diabetic and non-diabetic individuals, enabling high sensitivity and specificity in screening and monitoring applications.

Clinically, the system can be used as a screening tool for early metabolic abnormalities in undiagnosed patients, for non-invasive glucose monitoring to complement or reduce the need for finger-prick testing, to track ocular surface complications associated with diabetes, including dry eye syndrome and increased infection risk, and to detect inflammatory biomarkers linked to disease progression and therapeutic response The modular design also enables integration with telehealth platforms, making it suitable for remote monitoring in patients with limited access to clinical care. This repres innovation ents a transformative approach to chronic disease management, leveraging tear fluid as a real-time, biomolecular readout of systemic health.

Non-Invasive Glucose Monitoring and Mobile Integration

One of the more impactful applications of the AI-enhanced Raman spectroscopy tear analysis system 202 is its use for non-invasive glucose monitoring. The system detects Raman spectral shifts in the 1080-1120 $cm^{-1}$ region associated with glucose concentration in the tear film. Through routine sampling, the device can assess fluctuations in tear glucose, which correlate with systemic blood glucose levels.

In contrast to traditional glucometers requiring capillary blood via finger-prick, this AI-enhanced Raman spectroscopy tear analysis system 202 enables comfortable and contactless glucose assessment using ocular tear fluid. The AI module calibrates Raman spectral intensity against historical patterns for the individual patient, allowing personalized tracking of glycemic variation.

One innovation lies in the system's mobile integration capability. The diagnostic module communicates wirelessly with a dedicated smartphone application that serves as the user interface for:

- Real-time result display and glucose trend visualization
- Daily, weekly, and monthly glucose variability reports
- Alerts for hyperglycemic or hypoglycemic events based on customizable thresholds
- Data sharing with caregivers, clinicians, or cloud-based health record platforms The mobile application can be configured for both Android and iOS environments, using secure Bluetooth or Wi-Fi connections to receive and transmit data from the Raman device. Additionally, the application supports AI-driven insights and feedback loops, offering behavioral recommendations or reminders for measurement scheduling.

Through this integrated AI-enhanced Raman spectroscopy tear analysis system 202, patients with diabetes gain a powerful tool for home-based monitoring, while clinicians benefit from remote access to structured glucose reports and tear biomarker trends. This approach improves glycemic control, enhances patient compliance, and reduces dependence on invasive testing modalities.

Detection and Analysis of Tumor Biomarkers in Human Tears Using AI-Enhanced Raman Spectroscopy This embodiment describes a system and method for detecting tumor-associated biomarkers present in the tear film of a subject (human or non-human) using AI-Enhanced Raman spectroscopy. The AI-enhanced Raman spectroscopy tear analysis system 202 enables non-invasive assessment of ocular and systemic malignancies by identifying spectral features associated with tumor metabolism, oxidative stress, and immune activation.

Tears contain low concentrations of metabolites, proteins, lipids, and nucleic acid fragments that reflect both local ocular and systemic disease processes. In patients with malignancy, such as uveal melanomas, conjunctival carcinoma, or metastatic disease involving ocular tissue, Raman spectral analysis of tears reveals reproducible biochemical deviations from baseline. These deviations may include:

- Melanin and tryptophan-related peaks (e.g., 1370-1600 $cm^{-1}$, 1580 $cm^{-1}$)
- Nucleic acid vibrations (e.g., DNA/RNA backbone at ~785 and ~1330 $cm^{-1}$)
- Lactate (~845-875 $cm^{-1}$), indicative of anaerobic metabolism (Warburg effect)
- Altered lipid-to-protein ratios (~1450 and ~1655 $cm^{-1}$), suggestive of membrane remodeling
- Oxidative stress markers, such as cytochrome c and malondialdehyde (MDA, ~1720 $cm^{-1}$)
- Tumor-related enzymes, including tyrosinase and matrix metalloproteinase-9 (MMP-9)
- Pro-inflammatory cytokines, including interleukin-8 (IL-8)

The AI-enhanced Raman spectroscopy tear analysis system 202 directs a near-infrared laser 804 (e.g., 785 nm) toward the tear sample in vivo or in a microvolume collection vessel. Raman-scattered photons are collected by a spectral detection module and subjected to preprocessing to remove baseline fluorescence and normalize intensity. The processed spectra are analyzed using a convolutional neural network (CNN) trained on spectra from patients with and without confirmed ocular tumors.

The AI model extracts multi-dimensional spectral features and classifies samples using a softmax or ensemble learning framework. Diagnostic outputs may include malignancy probability scores, subtype differentiation (e.g., melanoma vs. carcinoma), and detection of tumor-associated inflammatory states.

The AI-enhanced Raman spectroscopy tear analysis system 202 has demonstrated the ability to distinguish tumor-bearing from control spectra based on spectral features in the regions of phenylalanine (~1005 $cm^{-1}$), nucleic acids (~1330 $cm^{-1}$), and melanin (~1580 $cm^{-1}$). These findings correlate with known hallmarks of cancer biology, including metabolic reprogramming, oxidative stress, and immune evasion.

This non-contact, tear-based method enables screening, adjunctive diagnosis, and monitoring of tumor presence or recurrence. When integrated into a longitudinal care plan, the AI-enhanced Raman spectroscopy tear analysis system 202 supports early detection and non-invasive surveillance, reducing reliance on more invasive or resource-intensive procedures.

Modularity and System Embodiments

The AI-enhanced Raman spectroscopy tear analysis system 202 is designed with a modular configuration that enables broad adaptability across diverse clinical, research, and telemedicine environments. The architecture separates the AI-enhanced Raman spectroscopy tear analysis system 202 into interoperable components, including the Raman module 206, AI processing unit 208, display screen 210 or interface module, power source, and tear collection device, each of which can be configured or interchanged depending on the intended use.

This modularity allows the AI-enhanced Raman spectroscopy tear analysis system 202 to be tailored for a range of physical embodiments, from handheld diagnostic tools to integrated bench-top analyzers. For example, the Raman module 206 (or Raman spectroscopy probe 826) may be implemented as a detachable module compatible with a slit lamp 204, or housed within a self-contained, portable unit for field-based diagnostics. The tear sampling component may range from contactless analysis of the tear meniscus to standardized cartridge-based sample collection, with the flexibility to accommodate patient preference or clinical workflow constraints.

The AI processing unit 208 may reside locally within the device or remotely via secure connection to a cloud-hosted environment, allowing scalable deployment in both offline and telehealth settings. Similarly, the interface module may include an onboard touchscreen display, mobile app, or EHR-integrated dashboard. This architecture supports plug-and-play replacement or upgrading of modules without requiring full system redesign, which facilitates maintenance, longevity, and customization.

To illustrate these variations, the following table summarizes exemplary modular configurations:

TABLE 26

Modular AI-Raman Spectroscopy Configurations

| Module | Function | Benefits | Interchangeable? | Notes |
|---|---|---|---|---|
| Spectroscopy Probe Module | Performs Raman data acquisition from tear film or ocular tissue | Allows different probe designs (e.g., for contactless use, integrated with slit lamp, or handheld) | Yes-swappable for different clinical contexts | |
| AI Interpretation Engine | Interprets spectral signatures using trained ML models | Updatable with new diagnostic algorithms and biomarker libraries | Yes-software-upgradable | |
| Display & Interface Module | Shows diagnostic output and recommendations | Enables use in standalone units or integrated with existing diagnostic systems | Yes-configurable with touchscreens, AR overlays, or EHR-linked displays | |
| Power & Data Transfer Module | Provides power and manages data flow (wired or wireless) | Enables portability and integration with cloud services | Yes-modular for clinical vs. field use | |
| Calibration and Reference Module | Ensures probe and signal consistency over time | Allows re-calibration using standard reference materials or internal calibration lasers | Yes-replaceable or software-triggered | |
| Diagnostic Cartridge (optional) | Preloaded tear film collection cartridge for single-use cases | Ensures sterility, standard volume, and reproducibility | Yes-consumable, case-dependent | |
| Cloud Sync & Normative Database Module | Compares with population-level data for risk stratification | Enhances decision support and AI model training | Yes-connected module or API-based | Local Storage, Bluetooth Sync, Secure Cloud Upload, Real-Time Mobile Sync |

This design allows the AI-enhanced Raman spectroscopy tear analysis system 202 to flexibly support diagnostics in ophthalmic clinics, remote care environments, high-throughput labs, and personalized home monitoring programs. By enabling clinicians and users to adapt the configuration to their needs, the AI-enhanced Raman spectroscopy tear analysis system 202 fosters greater accessibility, clinical utility, and long-term versatility.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies.

The foregoing devices and operations, including their implementation, will be familiar to, and understood by, those having ordinary skill in the art. This specification contains numerous dimensions, all of which could be changed without deviating from the inventions herein.

The above description of the embodiments, alternative embodiments, and specific examples, are given by way of illustration and should not be viewed as limiting. Further, many changes and modifications within the scope of the present embodiments may be made without departing from the spirit thereof, and the present inventions include such changes and modifications.

The invention claimed is:

1. A system for non-invasive biochemical analysis of tear film, comprising:

a Raman excitation source that directs light to the tear film of a subject and creates Raman-scattered light as the light reflects off the tear film;

a spectral acquisition module configured to detect the Raman-scattered light from the tear film, and create Raman spectral data from the Raman-scattered light; and a computer comprising one or more artificial intelligence (AI) models configured to preprocess, extract features from a Raman spectral data range of 1080-1120 $cm^{-1}$, and classify the Raman spectral data to identify one or more biomarkers associated with ocular or systemic disease.

2. The system of claim 1, wherein the one or more artificial intelligence (AI) models include a convolutional neural network (CNN) trained to classify spectral patterns in the Raman spectral data into diagnostic categories, including diabetes.

3. The system of claim 1, further comprising a longitudinal monitoring module configured to compare the Raman spectral data with previous Raman spectral data from the subject.

4. The system of claim 1, wherein the spectral acquisition module includes a non-contact optical head adapted for slit lamp integration to acquire Raman signals directly from the tear film.

5. The system of claim 1, further comprising a modular diagnostic cartridge containing a surface-enhanced Raman scattering (SERS) substrate and a tear-wicking membrane for collection of the tear film.

6. The system of claim 1, wherein the computer further comprises a segmentation module configured to identify spectral windows corresponding to known biomarkers including glucose.

7. The system of claim 1, wherein the one or more artificial intelligence (AI) models are configured to detect a level of glucose.

8. The system of claim 1, wherein the spectral acquisition module further comprises confocal optics for depth-resolved Raman signal capture.

9. The system of claim 1, wherein the one or more artificial intelligence (AI) models apply principal component analysis (PCA) or wavelet transforms for feature extraction.

10. The system of claim 1, wherein the one or more artificial intelligence (AI) models that classify are updated via encrypted cloud-based training, incorporating clinician feedback.

11. The system of claim 1, wherein the computer further includes a contextual data module configured to adjust classification thresholds based on time of day or environmental conditions.

12. The system of claim 1, further comprising a user interface that presents spectral trend graphs for tracked biomarkers across multiple visits.

13. The system of claim 1, further comprising a swept-source excitation module configured to dynamically tune laser wavelength based on target biomarker absorption characteristics.

14. The system of claim 1, wherein the one or more artificial intelligence (AI) models are further configured to determine diagnostic or monitoring results based on the one or more biomarkers, wherein the diagnostic or monitoring results include probability-weighted disease classifications and AI-generated treatment recommendations.

15. The system of claim 1, wherein the one or more artificial intelligence (AI) models are further configured to integrate Raman analysis results with ocular imaging data.

16. The system of claim 1, wherein the one or more artificial intelligence (AI) models are further configured to annotate the Raman spectral data with time-series metadata.

17. The system of claim 1, further comprising a mobile device platform housing the computer, the spectral acquisition module, and the Raman excitation source.

18. The system of claim 1, wherein the one or more artificial intelligence (AI) models are configured to denoise the Raman spectral data.

19. A method for diagnosing disease based on tear fluid analysis, comprising:

collecting a tear sample from a subject, illuminating the tear sample with a Raman excitation source;

detecting Raman-scattered light from the Raman excitation source reflected off of the tear sample;

converting the Raman-scattered light into spectral data; and processing the spectral data in a range of 1080-1120 $cm^{-1}$ using an AI model configured to classify the subject into one or more diagnostic categories.

20. The method of claim 19, wherein the AI model is configured to classify the subject as having an excessive level of glucose.

21. The method of claim 19, wherein the one or more diagnostic categories includes metabolic disorders.

22. The method of claim 19, wherein the tear sample are collected via Schirmer strip- or hydrogel pad.

23. The method of claim 19, wherein preprocessing includes baseline correction, Savitzky-Golay smoothing, and fluorescence suppression.

24. The method of claim 19, wherein classification is achieved using a random forest, support vector machine, or ensemble model.

25. A portable tear analysis device comprising:

a Raman spectroscopy module configured to direct light onto tear film of a subject, creates Raman-scattered light as the light reflects off the tear film, detects the Raman-scattered light from the tear film, and creates Raman spectral data from the Raman-scattered light;

a computer comprising one or more artificial intelligence (AI) models;

an AI processing unit housed within the portable tear analysis device configured to preprocess, extract features from a Raman spectral data range of 1080-1120 $cm^{-1}$, classify the Raman spectral data to identify one or more biomarkers associated with diabetes, and determine diagnostic or monitoring results based on the one or more biomarkers; and a display configured to output the diagnostic or monitoring results in real time to a clinician or the subject.

* * * * *